United States Patent
Chiocca et al.

(10) Patent No.: US 6,602,499 B1
(45) Date of Patent: Aug. 5, 2003

(54) COMBINATION VIRAL-BASED AND GENE-BASED THERAPY OF TUMORS

(75) Inventors: E. Antonio Chiocca, Brookline, MA (US); Xandra O. Breakefield, Newton, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/302,952

(22) Filed: Apr. 30, 1999

Related U.S. Application Data
(60) Provisional application No. 60/083,663, filed on Apr. 30, 1998.

(51) Int. Cl.[7] .................. A61K 35/00; A61K 48/00; C12N 15/63; C12N 5/00
(52) U.S. Cl. .................. 424/93.2; 424/93.1; 435/320.1; 435/325; 514/44
(58) Field of Search ................... 435/320.1; 514/44; 424/93.1, 93.2

(56) References Cited

U.S. PATENT DOCUMENTS

| | | | |
|---|---|---|---|
| 4,603,112 A | 7/1986 | Paoletti et al. | 435/235 |
| 5,288,641 A | 2/1994 | Roizman | 435/320 |
| 5,585,096 A | 12/1996 | Martuza et al. | 435/325 |
| 5,677,178 A | 10/1997 | McCormick | 514/44 |
| 5,688,773 A | 11/1997 | Chiocca et al. | 424/93.2 |
| 6,106,826 A | * 8/2000 | Brandt et al. | 424/93.2 |

FOREIGN PATENT DOCUMENTS

| | | |
|---|---|---|
| EP | 0 476 953 A2 | 3/1992 |
| EP | 0 514 603 A1 | 11/1992 |

OTHER PUBLICATIONS

Cheng et al. Proc. Natl. Acad. Sci. USA 94:690–694, 1997.*
Crystal RG. Science 270:404–410 1995.*
Verma IM and Somia N. Nature 389: 239–242. 1997.*
Kramm CM et al. Human Gene Therapy 7:1989–1994, 1996.*
Carroll NM et al. Annals of Surgery 224:323–330, 1996.*
Chen et al. Cancer Research 56: 1331–1340, 1996.*
Aghi M et al. Cancer Research 59:3861–3865, 1999.*
Database Medline on Dialog, Abstract for Breakfield, X.O. et al., "Gene therapy for brain tumors using herpes virus vectors (Meeting abstract)," *Ann. Oncol.* 7:23, abstract (1996).
Yamada, Y., et al., "The Pathogenicity of Ribnonucleotide Reductase–Null Mutants of Herpes Simplex Virus Type 1 in Mice," *J. Infect. Dis.* 164:1091–1097 (1991).
Virology, 3rd ed., Fields, B.N., Knipe, D.M., and Howley, P.M., eds., Lippincott–Raven Publishers, New York, vol. 2, pp. 2123–2126, 2346, 2452, 2529, and 2642 (1996).

(List continued on next page.)

*Primary Examiner*—Ram R. Shukla
(74) *Attorney, Agent, or Firm*—Sterne, Kessler, Goldstein & Fox P.L.L.C.

(57) ABSTRACT

The present invention relates to viral mutants and methods of using these viral mutants for selectively killing neoplastic cells. The viral mutants of the invention are capable of selectively killing neoplastic cells by a combination of viral mediated oncolysis and anti-cancer ("suicide") gene therapy.

30 Claims, 11 Drawing Sheets

OTHER PUBLICATIONS

Alavi, J.B, and Eck, S.L., "Gene Therapy for Malignant Gliomas," *Hematology/Oncology Clinics of North America* 12:617–629 (1998).

Carroll, N.M., et al., "The Effect of Ganciclovir on Herpes Simplex Virus–Mediated Oncolysis," *J. Surg. Res.* 69:413–417 (1997).

Cavazzana–Calvo, M., et al., "Gene Therapy of Human Severe Combined Immunodeficiency (SCID)–X1 Disease," *Science* 288:669–672 (Apr. 2000).

de Wind, N., et al., "Mutagenesis and Characterization of a 41–Kilobase–Pair Region of the Pseudorabies Virus Genome: Transcription Map, Search for Virulence Genes, and Comparison with Homologs of Herpes Simplex Virus Type 1," *Virology* 200:784–790 (1994).

Ganly, I., et al., "A Phase I Study of Onyx–015, an E1B Attenuated Adenovirus, Administered Intratumorally to Patients with Recurrent Head and Neck Cancer," *Clin. Cancer Res.* 6:798–806 (Mar. 2000).

Harsh, G.R., et al., "Thymidine kinase activation of ganciclovir in recurrent malignant gliomas: a gene–marking and neuropathological study," *J. Neurosurg.* 92:804–811 (May 2000).

Huang, A., et al., "Expression of the HSV–2 Ribonucleotide Reductase Subunits in Adenovirus Vectors or Stably Transformed Cells: Restoration of Enzymatic Activity by Reassociation of Enzyme Subunits in the Absence of Other HSV Proteins," *Virology* 163:462–470 (1988).

Ikeda, K., et al., "Oncolytic virus therapy of multiple tumors in the brain requires suppression of innate and elicited antiviral repsonses," *Nat. Med.* 5:881–887 (Aug. 1999).

Ikeda, K., et al., "Complement Depletion Facilitates the Infection of Multiple Brain Tumors by an Intravascular, Replication–Conditional Herpes Simplex Virus Mutant," *J. Virol.* 74:4765–4775 (May 2000).

Markert, J.M., et al., "Conditionally replicating herpes simplex virus mutant, G207 for the treatment of malignant glioma: results of phase I trial," *Gene Therapy* 7:867–874 (May 2000).

Martuza, R.L., "Conditionally replicating herpes vectors for cancer therapy," *J. Clin. Invest.* 105:841–846 (Apr. 2000).

Pawlik, T.M., et al., "Oncolysis of Diffuse Hepatocellular Carcinoma by Intravascular Administration of a Replication–competent, Genetically Engineered Herpesvirus," *Cancer Res.* 60:2790–2795 (Jun. 2000).

Rampling, R., et al., "Toxicity evaluation of replication–competent herpes simplex virus (ICP 34.5 null mutant 1716) in patients with recurrent malignant glioma," *Gene Therapy* 7:859–866 (May 2000).

Ausubel, F.M., et al., eds., "Protein Expression," Chapter 16 in *Short Protocols in Molecular Biology* ($4^{th}$ ed.), John Wiley & Sons, Inc., New York, NY, pp. 16–1–16–107 (Apr. 1999).

Bi, W.L., et al., "In Vitro Evidence That Metabolic Cooperation Is Responsible for the Bystander Effect Observed in HSV tk Retroviral Gene Therapy," *Human Gene Ther.* 4:725–731 (1993).

Bigner, D.D., et al., "Heterogeneity of Genotypic and Phenotypic Characteristics of Fifteen Permanent Cell Lines Derived from Human Gliomas," *J. Neuropathol. Exp. Neurol.* 40:201–229 (1981).

Bischoff, J.R., et al., "An Adenovirus Mutant That Replicates Selectivity in p53–Deficient Human Tumor Cells," *Science* 274:373–376 (1996).

Boviatsis, E.J., et al., "Long–Term Survival of Rats Harboring Brain Neoplasms Treated with Ganciclovir and a Herpes Simplex Virus Vector That Retains an Intact Thymidine Kinase Gene," *Cancer Res.* 54:5745–5751 (1994).

Breakefield, X.O. and Geller, A.I., "Gene Transfer into the Nervous System," *Molec. Neurobiol.* 1:339–371 (1987).

Burger, P.C., et al., "Computerized tomographic and pathologic studies of the untreated quiescent, and recurrent glioblastoma multiforme," *J. Neurosurg.* 58:159–169 (1983).

Cameron, J.M., et al., "Ribonucleotide Reductase Encoded by Herpes Simplex Virus Is a Determinant of the Pathogenicity of the Virus in Mice and a Valid Antiviral Target," *J. Gen. Virol.* 69:2607–2612 (1988).

Chambers, R. et al., "Comparison of genetically engineered herpes simplex viruses for the treatment of brain tumors in scid mouse model of human and malignant glioma," *Proc. Natl. Acad. Sci. USA* 92:1411–1415 (1995).

Chang, J.Y., et al.,"A Gene Delivery/Recall System for Neurons Which Utilizes Ribonucleotide Reductase–Negative Herpes Simplex Viruses," *Virol.* 185:437–440 (1991).

Chang, T.K.H., "Differential Activation of Cyclophosphamide and Ifosphamide by Cyclochromes P–450 2B and 3A in Human Liver Microsomes," *Cancer Res.* 53:5629–5637 (1993).

Chase, M. et al., "An oncolytic viral mutant that delivers the CYP2B1 transgene and augments cyclophosphamide chemotherapy," *Nat. Biotech.* 16:444–448 (1998).

Chen, S.–H. et al., "Gene therapy for brain tumors: Regression of experimental gliomas by adenovirus–mediated gene transfer in vivo," *Proc. Natl. Acad. Sci. USA* 91:3054–3057 (1994).

Chen, L. and Waxman, D.J., "Intratumoral Activation and Enhanced Chemotherapeutic Effect of Oxazaphosphorines following Cytochrome P–450 Gene Transfers: Development of a Combined Chemotherapy/Cancer Gene Therapy Strategy," *Cancer Res.* 55:581–589 (1995).

Chen, L., et al., "Sensitization of Human Breast Cancer Cells to Cyclophosphamide and Ifosamade by Transfer of a Liver Cytochrome P450 Gene," *Cancer Res.* 56:1331–1340 (1996).

Chou, J. and Roizman, B., "The $Y_1$ 34.5 gene of herpes simplex virus 1 precludes neuroblastoma cells from triggering total shutoff of protein synthesis characteristic of programmed cell death in neuronal cells," *Proc. Natl. Acad. Sci. USA* 89:3266–3270 (1992).

Christian, M.C., et al., "4–Ipomeanol: A Novel Investigational New Drug for Lung Cancer," *J. Natl. Cancer Inst.* 81:1133–1143 (1989).

Clarke, L. and Waxman, D.J., "Oxidative Metabolism of Cyclophosphamide: Identification of the Hepatic Monooxygenase Catalysts of Drug Activation," *Cancer Res.* 49:2344–2350 (1989).

Coen, D.M., et al., "A Genetic Approach to Promoter Recognition During trans Induction of Viral Gene Expression," *Science* 234:53–59 (1986).

Coen, D.M., "Molecular Genetics of Animal Viruses," Chapter 7 in *Fundamental Virology* (2nd ed.), Fields, B.N. et al., (eds.) Raven Press, New York, NY, pp. 123–151 (1990).

Coggins, C.A., et al., "Enhancement of irinotecan (CPT–11) activity against central nervous system tumor xenografts by alkylating agents," *Cancer Chemother. Pharmacol.* 41:485–490 (May 1998).

Colvin, M. and Hilton, J., "Pharmacology of Cyclophosphamide and Metabolites," *Cancer Treat. Rep.* 65(Suppl. 3):89–95 (1981).

Colvin, M., "Alkylating Agents and Platinum Antitumor Compounds," in *Cancer Medicine* (3rd ed.), vol. 1, Holland, J.F., et al., eds., Lea & Febiger, Philadelphia, PA, pp. 733–754 (1993).

Culver, K.W., "Clinical Applications of Gene Therapy for Cancer," *Clin. Chem.* 40:510–512 (1994).

Danks, M.K., et al., "Overexpression of a Rabbit Liver Carboxylesterase Sensitizes Human Tumor Cells in CPT–11," *Cancer Res.* 58:20–22 (Jan. 1998).

DeGregori, J., et al., "Cellular Targets for Activation by the E2F1 Transcription Factor Include DNA Synthesis—and $G_1S$–Regulatory Genes," *Mol. Cell. Biol.* 15:4215–4224 (1995).

DeLuca, N.A., et al., "Isolation and Characterization of Deletion Mutants of Herpes Simplex Virus Type 1 in the Gene Encoding Immediate–Early Regulatory Protein ICP4," *J. Virol.* 56:558–570 (1985).

Dutia, B.M., "Ribonucleotide Reductase Induced by Herpes Simplex Virus has a Virus–specified Constituent," *J. Gen. Virol.* 64:513–521 (1983).

Dynlacht, B.D., et al., "Differential regulation of E2F trans–activation by cyclin/cdk2 complexes," *Genes Dev.* 8:1772–1786 (1994).

Elion, G.B., "The biochemistry and mechanism of action of acyclovir," *J. Antimicrob. Chemother.* 12(Suppl. B):9–17 (1983).

Fakhrai, H., "Eradication of established intracranial rat gliomas by transforming growth factor β antisense gene therapy," *Proc. Natl. Acad. Sci. USA* 93:2909–2914 (1996).

Friedlos, F., et al., "Gene–directed enzyme prodrug therapy: quantitative bystander cytotoxicity and DNA damage induced by CB1954 in cells expressing bacterial nitroreductase," *Gene Ther.* 5:105–112 (Jan. 1998).

Gage, P.J., et al., "A Cell–Free Recombination System for Site–Specific Integration of Multigenic Shuttle Plasmids into the Herpes Simplex Virus Type 1 Genome," *J. Virol.* 66:5509–5515 (1992).

Genka, S., et al., "Brain and plasma pharmacokinetics and anticancer activities of cyclophosphamide and phosphoramide mustard in the rat," *Cancer Chemother. Pharmacol.* 27:1–7 (1990).

Glorioso, J.C., et al., "Herpes simplex virus–based vectors," *Seminars in Virol.* 3:265–276 (1992).

Goldstein, D.J. and Weller, S.K., "Factor(s) Present in Herpes Simplex Virus Type 1–Infected Cells Can Compensate for the Loss of the Large Subunit of the Viral Ribonucleotide Reductase: Characterization of an ICP6 Deletion Mutant," *Virol.* 166:41–51 (1988).

Goldstein, D.J. and Weller, S.K., "Herpes Simplex Virus Type 1–Induced Ribonucleotide Reductase Activity Is Dispensible for Virus Growth and DNA Synthesis: Isolation and Characterization of an ICP6 lacZ Insertion Mutant,"0 *J. Virol.* 62:196–205 (1988).

Göpferich, A., et al., "Development and Characterization of Microencapsulated Microspheres," *Pharma. Res.* 11:1568–1574 (1994).

Green, N.K. et al., "Sensitization of colorectal and pancreatic cancer cell lines to the prodrug 5–(aziridin–1–yl)–2, 4–dinitrobenzamide (CB1954) by retroviral transduction and expression of the *E. coli* nitroreductase gene," *Cancer Gene Ther.* 4:229–238 (Jul. 1997).

Hodgson, A.V., et al., "Expression analysis of the mixed function oxidase system in rat brain by the polymerase chain reaction," *Molec. Cell. Biochem.* 120:171–179 (1993).

Hossain, A., et al., "Analysis of cyclin–dependent kinase activity after herpes simplex virus type 2 infection," *J. Gen. Virol.* 78:3341–3348 (Dec. 1997).

Huang, H.–J.S., et al., "The Enhanced Tumorigenic Activity of a Mutant Epidermal Growth Factor Receptor Common in Human Cancers Is Mediated by Threshold Levels of Constitutive Tyrosine Phosphorylation and Unattenuated Signaling," *J. Biol. Chem.* 272:2927–2935 (Jan. 1997).

Huszar, D. and Bacchetti, S., "Partial Purification and Characterization of the Ribonucleotide Reductase Induced by Herpes Simplex Virus Infection of Mammalian Cells," *J. Virol.* 37:580–588 (1981).

Jacobson, J.G., et al., "A Herpes Simplex Virus Ribonucleotide Reductase Deletion Mutant Is Defective for Productive Acute and Reactivatable Latent Infections of Mice and for Replication in Mouse Cells," *Virol.* 173:276–283 (1989).

Jansen, W.J.M., et al., "CPT–11 in Human Colon–Cancer Cell Lines and Xenografts: Characterization of Cellular Sensitivity Determinants," *Int. J. Cancer* 70:335–340 (Jan. 1997).

Johnson, P.A. et al., "Cytotoxicity of a Replication–Defective Mutant of Herpes Simplex Virus Type 1," *J. Virol.* 66:2952–2965 (1992).

Kaplitt, M.G., et al., "Mutant herpes simplex virus induced regression of tumors growing in immunocompetent rats," *J. Neuro–Oncol.* 19:137–147 (1994).

Kesari, S., et al., "Therapy of Experimental Human Brain Tumors Using a Neuroattenuated Herpes Simplex Virus Mutant," *Lab. Invest.* 73:636–648 (1995).

Langer, R., "1994 Whitaker Lecture: Polymers for Drug Delivery and Tissue Engineering," *Ann. Biomed. Eng.* 23:101–111 (1995).

Le Blanc, G.A. and Waxman, D.J., "Interaction of Anticancer Drugs with Hepatic Monooxygenase Enzymes," *Drug Metabol. Rev.* 20:395–439 (1989).

Leib, D.A. and Olivo, P.D., "Gene Delivery to Neurons: Is Herpes Simplex Virus the Right Tool for the Job?," *BioEssays* 15:547–554 (1993).

Lorence, R.M., et al., "Complete Regression of Human Neuroblastoma Xenografts in Athymic Mice After Local Newcastle Disease Virus Therapy," *J. Natl. Cancer Inst.* 86:1228–1233 (1994).

Lukas, J., et al., "Deregulated Expression of E2F Family Members Induces S–Phase Entry and Overcomes p16$^{INK4A}$–Mediated Growth Suppression," *Molec. Cell. Biol.* 16:1047–1057 (1996).

Macdonald, J.S., et al., "Phase II evaluation of topotecan in patients with advanced colorectal cancer," *Invest. New Drugs* 15:357–359 (1997).

Marais, R., et al., "Gene–directed Enzyme Prodrug Therapy with a Mustard Prodrug/Carboxypeptidase G2 Combination," *Cancer Res.* 56:4735–4742 (1996).

Markert, J.M., et al., "Expanded spectrum of viral therapy in the treatment of nervous system tumors," *J. Neurosurg.* 77:590–594 (1992).

Markert, J.M., et al., "Reduction and Elimination of Encephalitis in an Experimental Glioma Therapy Model with Attenuated Herpes Simplex Mutants that Retain Susceptibility to Acyclovir," *Neurosurg.*32597–603 (1993).

Martuza, R.L., et al., "Experimental Therapy of Human Glioma by Means of a Genetically Engineered Virus Mutant," *Science* 252:854–856 (1991).

Matz, B., et al., "Physical Mapping of Temperature–sensitive Mutations of Herpes Simplex Virus Type 1 Using Cloned Restriction Endonuclease Fragments," *J. Gen. Virol.* 64:2261–2270 (1983).

McCarthy, A.M., et al., "Herpes Simplex Virus Type 1 ICP27 Deletion Mutants Exhibit Altered Patterns of Transcription and Are DNA Deficient," *J. Virol.* 63:18–27 (1989).

McLauchlan, J. and Clements, J.B., "Organization of the Herpes Simplex Virus Type 1 Transcription Unit Encoding Two Early Proteins with Molecular Weights of 140,000 and 40,000," *J. Gen. Virol.* 64:997–1006 (1983).

McLauchlan J. and Clements, J.B., "DNA sequence homology between two co–linear .loci on the HSV genome which have different transforming abilities," *EMBO J.* 2:1953–1961 (1983).

McGeoch, D.J., et al., "The Complete DNA Sequence of the Long Unique Region in the Genome of Herpes Simplex Virus Type 1," *J. Gen. Virol.* 69:1531–1574 (1988).

McGeoch, D.J., et al., "Complete DNA sequence of the short repeat region in the genome of herpes simplex virus type 1," *Nucl. Acids Res.* 14:1727–1745 (1986).

McGeoch, D.J., et al., "Sequence Determination and Genetic Content of the Short Unique Region in the Genome of Herpes Simplex Virus Type 1," *J. Mol. Biol.* 181:1–13 (1985).

Mineta, T., et al., "Treatment of Malignant Gliomas Using Ganciclovir–hypersensitive, Ribonucleotide Reductase–deficient Herpes Simplex Viral Mutant," *Cancer Res.* 54:3963–3966 (1994).

Mineta, T., et al., "CNS Tumor Therapy by Attenuated Herpes Simplex Viruses," *Gene Ther.* 1(Suppl. 1):s78 (1994).

Mineta, T., et al., "Attenuated multi–mutated herpes simplex virus–1 for the treatment of malignant gliomas," *Nat. Med.* 1:938–943 (1995).

Mocarski, E.S., "Molecular Engineering of the Herpes Simplex Virus Genome: Insertion of a Second L–S Junction into the Genome Causes Additional Genome Inversions," *Cell* 22:243–255 (1980).

Moolten, F.L., "Tumor Chemosensitivity Conferred by Inserted Herpes Thymidine Kinase Genes: Paradigm for a Prospective Cancer Control Strategy," *Cancer Res.* 46:5276–5281 (1986).

Moolten, F.L., et al., "Lymphoma Regression Induced by Ganciclovir in Mice Bearing a Herpes Thymidine Kinase Transgene," *Hum. Gene Ther.* 1:125–134 (1990).

Moolten, F.L. and Wells, J.M., "Curability of Tumors Bearing Herpes Thymidine Kinase Genes Transferred by Retroviral Vectors," *J. Natl. Cancer Inst.* 82:297–305 (1990).

Moolten, F.L., "Drug sensitivity ("suicide") genes for selective cancer chemotherapy," *Cancer Gene Therapy* 1:279–287 (1994).

Muldoon, L.L., et al., "Comparison of Intracerebral Inoculation and Osmotic Blood–Brain Barrier Disruption for Delivery of Adenovirus, Herpesvirus, and Iron Oxide Particles to Normal Rat Brain," *Am. J. Pathol.* 147:1840–1851 (1995).

Mullen, C.A., et al., "Transfer of the bacterial gene for cytosine deaminase to mammalian cells confers lethal sensitivity to 5–fluorocytosine: A negative selection system," *Proc. Natl. Acad. Sci. USA* 89:33–37 (1992).

Mroz, P.J. and Moolten, F.L., "Retrovirally Transduced *Escherichia coli* gpt Genes Combine Selectability with Chemosensitivity Capable of Mediating Tumor Eradication," *Hum. Gene Ther.* 4:589–595 (1993).

Nagane, M., et al., "A Common Mutant Epidermal Growth Factor Receptor Confers Enhanced Tumorigenicity on Human Glioblastoma Cells by Increasing Proliferation and Reducing Apoptosis," *Cancer Res.* 56:5079–5086 (1996).

Nagashima, T. and Hoshino, T., "Rapid Detection of S–Phase Cells by Anti–bromodeoxyuridine Monoclonal Antibody in 9L Brain Tumor Cells in vitro and in situ," *Acta Neuropathol.* 66:12–17 (1985).

Nelson, D.R., et al., "The P450 Superfamily: Update on New Sequences, Gene Mapping, Accession Numbers, Early Trivial Names of Enzymes, and Nomenclature," *DNA Cell Biol.* 12:1–51 (1993).

Nikas, I., et al., "Structural Features of Ribonucleotide Reductase," *Proteins: Structure, Function, and Genetics* 1:376–384 (1986).

Nilaver, G., et al.,"Delivery of herpesvirus and adenovirus to nude rat intercerebral tumors after osmotic blood–brain barrier disruption," *Proc. Natl. Acad. Sci. USA* 92:9829–9833 (1995).

Nishikawa, R., et al., "A mutant epidermal growth factor receptor common in human glioma confers enhanced tumorigenicity," *Proc. Natl. Acad. Sci. USA* 91:7727–7731 (1994).

Palella, T.D., et al., "Herpes Simplex Virus–Mediated Human Hypoxanthine–Guanine Phosphoribosyltransferase Gene Transfer into Neuronal Cells," *Molec. Cell. Biol.* 8:457–460 (1988).

Prigent, S. A., et al., "Enhanced Tumorigenic Behavior of Glioblastoma Cells Expressing a Truncated Growth Factor Receptor Is Mediated through the Ras–Shc–Grb2 Pathway," *J. Biol. Chem.* 271:25639–25645 (1996).

Oldfield, E. H., "Gene Therapy for the Treatment of Brain Tumors Using Intra–Tumoral Transduction with the Thymidine Kinase Gene and Intravenous Ganciclovir," *Hum. Gene Ther.* 4:39–69 (1993).

Perry, L. J. and McGeoch, D. J., "The DNA Sequences of the Long Repeat Region and Adjoining Parts of the Long Unique Region in the Genome of the Herpes Simplex Virus Type 1," *J. Gen. Virol.* 69:2831–2846 (1988).

Ram, Z., et al., "Summary of Results and Conclusion of the Gene Therapy of Malignant Brain Tumors: Clinical Study," *J. Neurosurg.* 82:343A (1995).

Ram, Z., et al., "Therapy of malignant brain tumors by intratumoral implantation of retroviral vector–producing cells," *Nat. Med.* 3:1354–1361 (Dec. 1997).

Rice, S. A. and Knipe, D. M., "Genetic Evidence for Two Distinct Transactivation Functions of the Herpes Simplex Virus α Protein ICP27," *J. Virol.* 64:1704–1715 (1990).

Rice, S. A., et al.,"The Acidic Amino–Terminal Region of Herpes Simplex Virus Type 1 Alpha Protein ICP27 Is Required for an Essential Lytic Function," *J. Virol.* 67:1778–1787 (1993).

Rodriguez, R., et al., "Prostate Attenuated Replication Competent Adenovirus (ARCA) CN706: A Selective Cytotoxic for Prostate–specific Antigen–positive Prostate Cancer Cells," *Can. Res.* 57:2559–2563 (Jul. 1997).

Roizman, B. and J. F. Jenkins,. "Genetic Engineering of Novel Genomes of Large DNA Viruses," *Science* 229:1208–1214 (1985).

Roth, J. A., et al., "Retrovirus–mediated wild–type p53 gene transfer to tumors of patients with lung cancer," *Nat. Med.* 2:985–991 (1996).

Shih, M.–F., et al.. "Herpes Simplex Virus as a Vector for Eukaryotic Viral Genes," *Vaccines 85* Cold Spring Harbor Laboratory, pp. 177–180 (1985).

Sidransky, D., et al., "Clonal expansion of p53 mutant cells is associated with brain tumor progression," *Nature* 355:846–847 (1992).

Sladek, N. E., "Oxazaphosphorines," in *Metabolism and Action of Anti–cancer Drugs,* Powis, G. and Prough, R. A. (eds.), Taylor and Francis, London, pp. 48–90 (1987).

Smith, P.B., et al., "4–Ipomeanol and 2–Aminoanthracene Cytotoxicity in C3H/10T1/2 Cells Expressing Rabbit Cytochrome P450 4B1," *Biochem. Pharmacol.* 50:1567–1575 (1995).

Smith, B.R. and Brian, W. R., "The Role of Metabolism in Chemical–Induced Pulmonary Toxicity," *Toxicol. Pathol.* 19:470–481 (1991).

Spaete, R.R.. and Frenkel, N., "The Herpes Simplex Virus Amplicon: A New Eucaryotic Defective–Virus Cloning–Amplifying Vector," *Cell* 30:295–304 (1982).

Swain, M. A. and Galloway, D. A., "Herpes Simplex Virus Specifies Two Subunits of Ribonucleotide Reductase Encoded by 3'–Coterminal Transcripts," *J. Virol.* 57:802–808 (1986).

Sze, P. and Herman, R. C., "The herpes simplex virus type 1 ICP6 gene is regulated by a 'leaky' early promoter," *Virus Res.* 26:141–152 (1992).

Tamargo, R. J., et al., "Interstitial Chemotherapy of the 9L Gliosarcoma: Controlled Release Polymers for Drug Delivery in the Brain," *Can. Res.* 53:329–333 (1993).

Ueki, K., et al., "CDKN2/p16 or RB Alterations Occur in the Majority of Glioblastomas and Are Inversely Correlated," *Can Res.* 56:150–153 (1996).

Vallette, F., et al., "Construction of mutant and chimeric genes using the polymerase chain reaction," *Nucl. Acid. Res.* 17:723–733 (1989).

Van Meir, E. G., et al., "Analysis of the p53 Gene and Its Expression in Human Glioblastoma Cells," *Can. Res.* 54:649–652 (1994).

Verschoyle, R.D., et al., "CYP4B1 Activates 4–Ipomeanol in Rat Lung," *Toxicol. Appl. Pharmacol.* 123:193–198 (1993).

Waxman, D. J., "Rat Hepatic Cytochrome P–450 Isoenzyme 2c," *J. Biol. Chem.* 259:15481–15490 (1984).

Waxman, D. J. and Walsh, C., "Phenobartibal–induced Rat Liver Cytochrome P–450," *J. Biol. Chem.* 257:10446–10457 (1982).

Weber, G. F. and Waxman, D. J., "Activation of the Anti–Cancer Drug Ifosphamide by Rat Liver Microsomal P450 Enzymes," *Biochem. Pharmacol.* 45:1685–1694 (1993).

Wei, M. X., et al., "Diffusible Cytotoxic Metabolites Contribute to the in Vitro Bystander Effect Associated with the Cyclophosphamide/Cytochrome P450 281 Cancer Gene Therapy Paradigm," *Clin. Can. Res.* 1:1171–1177 (1995).

Wei, M. X., et al., "Experimental Tumor Therapy in Mice Using the Cyclophosphamide–Activating Cytochrome P450 2B1 Gene," *Hum. Gene Ther.* 5:969–978 (1994).

Weizsaecker, M., et al., "The 9L Rat Brain Tumor: Description and Application of an Animal Model," *J. Neurol.* 224:183–192 (1981).

Wowra, B., et al., "Incidence of Late Radiation Necrosis with Transient Mass Effect After Interstitial Low Dose Rate Radiotherapy for Cerebral Gliomas," *Acta Neurochir. (Wien)* 99:104–108 (1989).

Yamano, S., et al., "The CYP2A3 Gene Product Catalyzes Coumarin 7–Hydroxylation in Human Liver Microsomes," *Biochem.* 29:1322–1329 (1990).

Yamano, S., et al., "cDNA Cloning and Sequence and cDNA–Directed Expression of Human P450 IIB1: Identification of a Normal and Two Variant cDNAs Derived from the CYP2B Locus on Chromosome 19 and Differential Expression of the IIB mRNAs in Human Liver," *Biochem.* 28:7340–7348 (1989).

Yoshii, Y., et al., "Estimation of growth fraction with bromodeoxyuridine in human central nervous system tumors," *J. Neurosurg.* 65:659–663 (1986).

Zamorano, L., et al.,"Tumor Recurrence vs. Radionecrosis: an Indication for Multitrajectory Serial Stereotactic Biopsies," *Acta Neurochir. Suppl.* 46:90–93 (1989).

Breakefield, X.O. and DeLuca, N.A., "Herpes Simplex Virus for Gene Delivery to Neurons," *New Biol.* 3:203–218 (1991).

Brem, H., "Polymers to treat brain tumors," *Biomat.* 11:699–701 (1990).

Buahin, K.G. and Brem, H., "Interstitial chemotherapy of experimental brain tumors: comparison of intratumoral injection versus polymeric controlled release," *J. Neuro–Oncol.* 26:103–110 (1995).

* cited by examiner

COMBINATION VIRAL-BASED AND GENE-BASED THERAPY OF TUMORS

CROSS REFERENCE TO RELATED APPLICATIONS

This application claims the benefit of U.S. Provisional Application No. 60/083,663, filed on Apr. 30, 1998, which is herein incorporated by reference.

STATEMENT AS TO RIGHTS TO INVENTIONS MADE UNDER FEDERALLY-SPONSORED RESEARCH AND DEVELOPMENT

At least part of the work performed during development of this invention utilized a grant from the National Cancer Institute, Grant No. CA69246-02. The U.S. Government has certain rights in this invention.

BACKGROUND OF THE INVENTION

1. Field of the Invention

The present invention relates to a viral mutant capable of selectively killing tumor cells. More particularly, the present invention relates to a viral mutant capable of selectively killing tumor cells by a combination of viral mediated oncolysis and anti-cancer ("suicide") gene therapy.

2. Related Art

A. Conventional Cancer Therapies

Neoplasia is a process that occurs in cancer, by which the normal controlling mechanisms that regulate cell growth and differentiation are impaired, resulting in progressive growth. This impairment of control mechanisms allows a tumor to enlarge and occupy spaces in vital areas of the body. If the tumor invades surrounding tissue and is transported to distant sites it will likely result in death of the individual.

In 1999, in the United States alone, approximately 563,100 people, or about 1,500 people per day, are expected to die of cancer. (Landis, et al., "Cancer Statistics, 1999, " *CA Canc. J. Clin.* 49:8–31 (1999)). Moreover, cancer is a leading cause of death among children aged 1 to 14 years, second only to accidents. Id. Thus, clearly there is a need for the development of new cancer therapies.

1. Common Limitations of Conventional Therapies

The desired goal of cancer therapy is to kill cancer cells preferentially, without having a deleterious effect on normal cells. Several methods have been used in an attempt to reach this goal, including surgery, radiation therapy, and chemotherapy.

Surgery was the first cancer treatment available, and still plays a major role in diagnosis, staging, and treatment of cancer, and may be the primary treatment for early cancers (see Slapak, C. A., and Kufe, D. W., "Principles of Cancer Therapy," in *Harrison's Principles of Internal Medicine*, Fauci, A. S. et al., eds., 14th Ed., McGraw-Hill Cos., Inc., New York, 1998, at 524). However, although surgery may be an effective way to cure tumors confined to a particular site, these tumors may not be curable by resection due to micrometastatic disease outside the tumor field. Id. Any cancer showing a level of metastasis effectively cannot be cured through surgery alone. Id.

Radiation therapy is another local (nonsystemic) form of treatment used for the control of localized cancers. Id. at 525. Many normal cells have a higher capacity for intercellular repair than neoplastic cells, rendering them less sensitive to radiation damage. Radiation therapy relies on this difference between neoplastic and normal cells in susceptibility to damage by radiation, and the ability of normal organs to continue to function well if they are only segmentally damaged. Id. Thus, the success of radiation therapy depends upon the sensitivity of tissue surrounding the tumor to radiation therapy. Id. Radiation therapy is associated with side effects that depend in part upon the site of administration, and include fatigue, local skin reactions, nausea and vomiting. Id. at 526. In addition, radiation therapy is mutagenic, carcinogenic and teratogenic, and may place the patient at risk of developing secondary tumors. Id.

Other types of local therapy have been explored, including local hyperthermia (Salcman et al., *J Neuro-Oncol.* 1:225–236 (1983)), photodynamic therapy (Cheng et al, *Surg. Neurol.* 25:423–435 (1986)), and interstitial radiation (Gutin et al., *J. Neurosurgery* 67:864–873 (1987)). Unfortunately, thus far these therapies have been met with only moderate success.

Local treatments, such as radiation therapy and surgery, offer a way of reducing the tumor mass in regions of the body that are accessible through surgical techniques or high doses of radiation therapy. However, more effective local therapies with fewer side effects are needed. Moreover, these treatments are not applicable to the destruction of widely disseminated or circulating tumor cells eventually found in most cancer patients. To combat the spread of tumor cells, systemic therapies are used.

One such systemic treatment is chemotherapy. Chemotherapy is the main treatment for disseminated, malignant cancers. (Slapak, C. A., and Kufe, D. W., "Principles of Cancer Therapy," in *Harrison's Principles of Internal Medicine*, Fauci, A. S. et al., eds., 14th Ed., McGraw-Hill Cos., Inc., New York, 1998, 527). However, chemotherapeutic agents are limited in their effectiveness for treating many cancer types, including many common solid tumors. See id This failure is in part due to the intrinsic or acquired drug resistance of many tumor cells. See id. at 533. Another drawback to the use of chemotherapeutic agents is their severe side effects. See id. at 532. These include bone marrow suppression, nausea, vomiting, hair loss, and ulcerations in the mouth. Id. Clearly, new approaches are needed to enhance the efficiency with which a chemotherapeutic agent can kill malignant tumor cells, while at the same time avoiding systemic toxicity.

2. Challenges Presented by Central Nervous System Tumors

Another problem presented in cancer treatment is that certain types of cancer, e.g., gliomas, which are the most common primary tumor arising in the human brain, defy the current modalities of treatment. Despite surgery, chemotherapy, and radiation therapy, glioblastoma multiforme, the most common of the gliomas, is almost universally fatal (Schoenberg, in *Oncology of the Nervous System*, M. D. Walker, ed., Boston, Mass., Martinus Nijhoff (1983); Levin et al., Chapter 46 in *Cancer: Principles and Practice of Oncology*, vol. 2, 3rd ed., De Vita et al., eds., Lippincott Press, Philadelphia (1989), pages 1557–1611).

Gliomas represent nearly 40% of all primary brain tumors, with glioblastoma multiforme constituting the most malignant form (Schoenberg, "The Epidemiology of Nervous System Tumors," in *Oncology of the Nervous System*, Walker, ed., Cold Spring Harbor Laboratory, Cold Spring Harbor, N.Y. (1983)). The five year survival rate for persons with this high grade type of astrocytoma is less than 5 percent, given the current treatment modalities (surgery, radiation therapy and/or chemotherapy) (Mahaley et al., *Neurosurgery* 71: 826–836 (1989); Schoenberg, in *Oncology of the Nervous System*, Walker, ed., Cold Spring Harbor Laboratory, Cold Spring Harbor, N.Y. (1983); Kim et al., *J.*

Neurosurg. 74:27–37 (1991), Daumas-Duport et al., *Cancer* 2:2152–2165 (1988)). After treatment with radiation therapy, glioblastomas usually recur locally. Hochberg et al., *Neurology* 30: 907 (1980). Neurologic dysfunction and death in an individual with glioblastoma are due to the local growth of the tumor. Systemic metastases are rare. Id. For this reason, regional cancer therapy methods, rather than systemic methods, may be especially suitable for the treatment of glioblastomas.

Moreover, glioblastomas are resistant to many chemotherapeutic agents, perhaps due to the proliferative characteristics of this tumor type. Many chemotherapeutic agents are cell-cycle-active, i.e., cytotoxic primarily to actively cycling cells (Slapak, C. A., and Kufe, D. W., "Principles of Cancer Therapy," in *Harrison's Principles of Internal Medicine*, Fauci, A. S. et al., eds., 14th Ed., McGraw-Hill Cos., Inc., New York, 1998, 527). Generally, chemotherapy is most effective for cancers-with a small tumor burden where the growth fraction of the tumor is maximal. Id. The growth fraction for glioblastoma tumors is only 30%, with the remaining 70% of cells being in $G_0$, a resting phase (cells in $G_0$ may die or may re-enter the active cell cycle; Yoshii et al., *J. Neurosurg.* 65:659–663 (1986)). While the 30% of glioblastoma cells that are actively dividing contribute to the lethal progression of this tumor, the 70% that are quiescent are responsible for the resistance of these tumors to a number of chemotherapeutic agents that target actively proliferating cells.

Unfortunately, regional treatments, such as surgery and radiation therapy have also found limited success in the treatment of glioblastomas. (Burger et al., *J. Neurosurg.* 58:159–169 (1983); Wowra et al., *Acta Neurochir.* (Wien) 99:104–108 (1989); Zamorano et al., *Acia Neurochir. Suppl.* (Wien) 46:90–93 (1989)). Surgical treatment methods for glioblastomas are hampered by the lack of distinct boundaries between the tumor and the surrounding parenchyma, and by the migration of tumor cells in the white matter tracts extending out from the primary site (Burger et al., *J. Neurosurg.* 58:159–169 (1983)), which preclude their complete removal. Radiation therapy, which targets rapidly proliferating cells, is limited by the low growth fraction in glioblastomas, and by the radiation sensitivity of adjacent normal tissue (Wowra et al., *Acta Neurochir.* (Wien) 99:104–108 (1989); Zamorano et al., *Acta Neurochir. Suppl.* (Wien) 46:90–93 (1989)). Thus, new approaches are needed to treat brain tumors.

B. Non-traditional Cancer Therapy Approaches

One non-traditional therapeutic method employs viruses to target neoplastic cells. Proposed viral cancer therapies include two distinct approaches: (i) direct cell killing (oncolysis) by a mutagenized virus (Martuza et al., *Science* 252:854–856 (1991); Mineta et al., *Nature Med* 1:938–943 (1995); Boviatsis et al., *Cancer Res.* 54: 5745–5751 (1994); Kesari, et al., *Lab. Invest.* 73: 636–648 (1995); Chambers et al., *Proc. Natl. Acad. Sci. USA* 92: 1411–1415 (1995); Lorence, R. M. et al., *J. Natl. Cancer. Inst.* 86: 1228–1233 (1994); Bischoff, et al., Science 274: 373–376 (i996); Rodriguez et al., *Cancer Res.* 57: 2559–2563 (1997)), and (ii) the use of viral vectors to deliver a transgene whose expression product activates a chemotherapeutic agent (Wei et al., *Human Gene Therapy* 5: 969–978(1994); Chen and Waxman, *Cancer Res.* 55: 581–589 (1995); Moolten, *Cancer Gene Ther.* 1: 279–287 (1994); Fakhrai et al., *Proc. Natl. Acad. Sci. USA* 93: 2909–2914 (1996); Roth et al., *Nature Med.* 2: 985–991 (1996); Moolten, *Cancer Res.* 46: 5276–5281 (1986); Chen et al., *Proc. Natl. Acad. Sci. USA* 91: 3054–3057 (1994)).

1. Viral Oncolysis

With regard to the first approach in viral cancer therapy, viral oncolysis, the genetic engineering of viruses for use as oncolytic agents has initially focused on the use of replication-incompetent viruses. This strategy was hoped to prevent damage to non-tumor cells by the viruses. A major limitation of this approach is that these replication-incompetent viruses require a helper virus to be able to integrate and/or replicate in a host cell. One example of the viral oncolysis approach, the use of replication-defective retroviruses for treating nervous system tumors, requires the implantation of a producer cell line to spread the virus. These retroviruses are limited in their effectiveness, because each replication-defective retrovirus particle can enter only a single cell and cannot productively infect others thereafter. Therefore, they cannot spread far from the producer cell, and are unable to completely penetrate a deep, multilayered tumor in vivo. Markert et al., *Neurosurg.* 77: 590 (1992) Ram et al., *Nature Medicine* 3:1354–1361 (1997).

More recently, genetic engineering of oncolytic viruses has focused on the generation of "replication-conditional" viruses in an attempt to avoid systemic infection, while allowing the virus to spread to other tumor cells. Replication-conditional viruses are designed to preferentially replicate in actively dividing cells, such as tumor cells. Thus, these viruses should target tumor cells for oncolysis, and replicate in these cells so that the virus can spread to other tumor cells.

Some recent strategies for creating replication-conditional viral mutants as novel anticancer agents have employed mutations in selected adenoviral or herpes simplex virus type 1 (HSV-1) genes to render them viral replication-conditional (Martuza et al, *Science* 252:854–856 (1991); Mineta et al., *Nature Med* 1:938–943 (1995); Boviatsis et al., *Cancer Res.* 54: 5745–5751 (1994); Kesari, et al., *Lab. Invest.* 73: 636–648 (1995); Chambers et al., *Proc. Natl. Acad Sci. USA* 92: 1411–1415 (1995); Lorence, R. M. et al., *J. Natl. Cancer. Inst.* 86: 1228–1233 (1994); Bischoff, et al., *Science* 274: 373–376 (1996); Rodriguez et al., *Cancer Res.* 57: 2559–2563 (1997)). For example, an adenovirus with a deletion in the E1B-55Kd encoding gene has been shown to selectively replicate in p53-defective tumor cells (Bischoff, et al., *Science* 274: 373–376 (1996)). HSV-1 with deletions or insertions in viral genes encoding for thymidine kinase (Hstk) (Martuza et al., *Science* 252:854–856 (1991)), or ribonucleotide reductase (Hsrr) (Goldstein and Weller, *J. Virol.* 62: 196–205 (1988); Mineta et al., *Gene Therapy* 1:S78 (1994), Mineta et al., *J. Neurosurg.* 80:381 (1994); Mineta et al., *Nature Med* 1: 938–943 (1995); Boviatsis et al., *Cancer Res.* 54: 5745–5751 (1994)), or $\gamma_{34.5}$ (Mineta et al., *Nature Med* 1:938–943 (1995); Chambers et al., *Proc. Natl. Acad. Sci. USA* 92: 1411–1415 (1995)), have also been shown to replicate in and lyse dividing cells but not quiescent cells, presumably because the former can complement the defective viral function (Goldstein and Weller, *J. Virol.* 62: 196–205 (1988)).

However, these replication-conditional viral mutants have drawbacks. For example, the thymidine kinase deficient (TK–), viral mutant described by Martuza et al. (called dlsptk) (*Science* 252:854–856 (1991)), is only moderately attenuated for neurovirulence and produced encephalitis at the doses required to kill the tumor cells adequately (Markert et al., *Neurosurgery* 32:597 (1993)). Residual neurovirulence, as evidenced by a 50% lethality of intracranially-administered, replication-deficient herpes simplex virus viral vectors at $10^6$ plaque forming units (pfu), limits the use of such vectors for tumor therapy.

Furthermore, known TK− HSV-1 mutants are insensitive to acyclovir and ganciclovir, the most commonly used and efficacious anti-herpetic agents, and thus undesired viral spread cannot be controlled using these drugs.

Moreover, the HSV-1 RR− mutant with insertion of an *Escherichia coli* lacZ gene into the large subunit (ICP6) of Hsrr described by Goldstein and Weller, *J. Virol.* 62: 196–205 (1988), may be susceptible to spontaneous regeneration of the wild-type viral gene, which would render the virus replication competent in normal cells. An alternative ICP6 HSV-1 mutant, which is described in U.S. Pat. No. 5,585,096, was designed to contain a deletion mutation in the $_\gamma$34.5 gene in addition to the insertion of lacZ into ICP6, because the chance of reversion to the wild-type gene is smaller for a large deletional or substitutional mutation than for an insertional mutation. However, the oncolytic effect of both of these RR mutants, and other replication-conditional mutants that require cellular complementation of some factor for replication, is limited by tumor cell heterogeneity (Sidranski et al., 355: 846–847 (1992); Bigner et al, *J. Neuropathol. Exp. Neurol.* 40: 201–229 (1981)) for the cellular factor(s) necessary to complement the deficiencies of the viral mutant. Moreover, the viral oncolysis based approaches discussed above are limited by antiviral immune responses, as well as the possibility of host fever interfering with viral replication (for temperature sensitive mutants).

2. Viral Delivery of Anticancer Transgenes

As mentioned above, the second approach in viral cancer therapy is the viral delivery of anticancer transgenes (Wei et al., *Human Gene Therapy* 5: 969–978 (1994); Chen and Waxman, *Cancer Res.* 55: 581–589 (1995); Moolten, *Cancer Gene Ther.* 1: 279–287 (1994); Fakhrai et al., *Proc. Natl. Acad. Sci. USA* 93: 2909–2914 (1996); Roth et al., *Nature Med.* 2: 985–991 (1996); Moolten, *Cancer Res.* 46: 5276–5281 (1986); Chen et al., *Proc. Natl. Acad. Sci. USA* 91: 3054–3057 (1994); Mroz, and Moolten, *Hum. Gene Ther.* 4: 589–595 (1993); Mullen et al., *Proc. Natl. Acad. Sci. USA* 59: 33–37 (1992); Wei et al., *Clin. Cancer Res.* 1: 1171–1177 (1995); Marais et al., *Cancer Res.* 56: 4735–4742 (1996); Chen et al, *Cancer Res.* 56: 1331–1340 (1996)). It has been proposed that genes with a drug-conditional "killing" function (also referred to as suicide genes) be employed for treating tumors.

In one example of viral delivery of a suicide gene, expression of the HSV thymidine kinase (Hstk) gene in proliferating cells, was found to render cells sensitive to the deoxynucleoside analog, ganciclovir (GCV) (Moolten et al, *Cancer Res.* 46:5276–5281 (1986); Moolten et al., *Hum. Gene Ther.* 1:125–134 (1990); Moolten et al., *J. Natl. Cancer Inst.* 82:297–300 (1990)). HSV-TK mediates the phosphorylation of GCV, which is incorporated into DNA strands during DNA replication (S-phase) in the cell cycle, leading to chain termination and cell death (Elion, G. B., *J. Antimicr. Chemother.* 12, sup. B:9–17 (1983)). Cells bearing a retroviral vector carrying HSV-TK and implanted into brain tumors growing in human patients have been demonstrated to confer sensitivity to the anti-herpes drug GCV (Oldfield et al., *Hum. Gene Ther.* 4:39 (1993)). Of eight patients with recurrent glioblastoma multiforme or metastatic tumors treated by stereotactic implantation of murine fibroblast cells producing these retroviral vectors, five patients demonstrated some evidence of anti-tumor efficacy but none were cured (Culver, *Clin. Chem* 40: 510 (1994)).

These retroviral vectors are replication-incompetent, therefore viral spread is dependent on the implantation of a producer cell line. Thus, this type of viral therapy is subject to the following limitations: (1) low viral titer; (2) limitation of viral spread to the region surrounding the producer cell implant; (3) possible immune response to the producer cell line; (4).possible insertional mutagenesis and transformation of retroviral infected cells; (5) single treatment regimen of the pro-drug, GCV, because the "suicide" product kills retrovirally infected cells and producer cells; and (6) limitation of the bystander effect to cells in direct contact with retrovirally transformed cells (Bi et al., *Human Gene Therapy* 4: 725 (1993)). Oldfield et al. (1993), supra. In addition, for therapies using drugs such as GCV, the dependence on the occurrence of DNA replication during drug exposure may limit its therapeutic effectiveness. For instance, because the majority of cells in human malignant brain tumors are in $G_0$ (resting phase) at any one time (Nagashima et al., *Acta Neuropathol.* 66:12–17 (1985); Yoshii et al., *J. Neurosurg.* 65:659–663 (1986)), the majority of cells would not be targeted by transient exposure to the drug.

Another example of a suicide gene suitable for viral delivery is the cytochrome P450 gene, which confers chemosensitivity to the class of oxazaphosphorine drugs. Two of these drugs, cyclophosphamide (CPA) and its isomeric analog ifosfamide (IFA) are mainstays of cancer chemotherapy for several types of tumors (Colvin, O. M., in *Cancer Medicine*, Holland et al., eds., Lea and Febiger, Philadelphia, Pa. (1993), pages 733–734). These therapeutically inactive prodrugs require bioactivation by liver-specific enzymes of the cytochrome P450 family. One of these enzymes, cytochrome P450 2B1 ("CYP2B1"), which is induced by phenobarbital, activates CPA and IFA with high efficiency (Clarke et al., *Cancer Res.* 49:2344–2350 (1989); Weber and Waxman, *Biochem. Pharm.* 45:1685–1694 (1993)). CPA and IFA are hydroxylated by cytochrome P450 to yield the primary metabolites, 4-hydroxycyclophosphamide or 4-hydroxyifosphamide, respectively. These primary metabolites are unstable and spontaneously decompose into cytotoxic compounds: acrolein and phosphoramide (or ifosphoramide) mustard (Colvin et al., *Cancer Treat. Rep.* 65:89–95 (1981); Sladek, in *Metabolism and Action of Anticancer Drugs*, Powis et al., eds., Taylor and Francis, New York (1987), pages 48–90). The latter causes interstrand cross-links in DNA regardless of cell-cycle phase. Maximum cytotoxicity is obtained during subsequent synthesis (S) and mitotic (M)-phases of the cell cycle due to strand breaks (Colvin (1993), supra). U.S. Pat. No. 5,688,773, to Chiocca et al. (Nov. 18, 1997), describes a gene therapy paradigm using cytochrome P450 and CPA.

The inventors and others have employed replication-defective vectors based on retrovirus (Wei et al., *Human Gene Therapy* 5: 969–978 (1994); Chiocca et al., U.S. Pat. No. 5,688,773), or adenovirus (Chen et al., *Cancer Res.* 56: 1331–1340 (1996)) to achieve transfer into tumor cells of the transgene encoding rat CYP2B1. When treated with CPA, tumor cells engineered to express cytochrome CYP2B1 generate freely diffusible active CPA metabolites that are cytotoxic to surrounding tumor cells, which may not contain the CYP2B1 transgene (Chen and Waxman, *Cancer Res.* 55: 581–589 (1995); Wei et al., *Clin. Cancer Res.* 1: 1171–1177 (1995)). Thus, the CPA/cytochrome P450 gene therapy approach may provide a means for intratumoral generation of alkylating metabolite.

Without the expression of P450 to provide local activation, conversion of oxazaphosphorine anti-cancer drugs, such as CPA, into their active metabolites is primarily restricted to the liver. Thus, typically, the active metabolites, are distributed systemically. Due to the toxicity of the active metabolites, oxazaphosphorine drugs may not be able to be administered at sufficiently high levels to effectively kill the tumor, without also causing systemic toxicity in the patient, and possibly death. Moreover, oxazaphosphorines are largely ineffective in treating tumors of the central nervous system (CNS) owing to the poor transport of the activated metabolites across the blood-brain barrier and into cells (Genka et al., *Cancer Chemother. Pharmacol.* 27:1–7 (1990)), and to the low levels of cytochrome P450 found in brain and tumor cells (Hodgson et al., *Mol. Cell. Biochem.* 120:171–179(1993)).

Thus, one benefit of the CPA/cytochrome P450 gene therapy approach is the intratumoral generation of alkylating metabolite. By providing elevated concentrations of the anticancer agent in the tumor, this approach may reduce the exposure of normal cells to toxic metabolites and thus reduce the amount of drug required to be administered. However, none of the gene based approaches presently available, including the CPA/CYP2B1 paradigm described above, offer the benefit of combined viral mediated oncolysis with suicide gene mediated oncolysis.

While both the virus-based and the gene-based approaches have provided evidence of significant therapeutic effects in animal models of tumors, each method suffers from inherent limitations. Although the virus-based approach theoretically provides the potential for extensive replication of the virus with spread in the tumor mass, its effects are limited by the efficiency of viral infection; the requirement of a helper virus or producer cell line for some viral vectors; tumor cell heterogeneity (Sidranski et al., 355: 846–847 (1992); Bigner et al, *J. Neuropathol. Exp. Neurol.* 40: 201–229 (1981)) for the cellular factor(s) complementing viral mutant growth for other viral vectors; and antiviral immune responses.

In the gene-based approaches tested thus far, the efficiency of transduction of cells within a tumor mass is limited by the defective nature of the vector. In fact, the majority of positively transduced cells occurs within a few cell layers from the site of vector inoculation (Nilaver et al. *Proc. Natl. Acad. Sci. USA* 21: 9829–9833 (1995); Muldoon et al., *Am. J. Pathol.* 147: 1840–1851 (1995); Ram Z. et al., *J. Neurosurg.* 82, 343A (abst.)(1995)). Moreover, even for viral vector systems where a producer cell line is unnecessary, or not killed by the suicide gene/drug combination, viral replication may be inhibited by the drug used. Furthermore, where the suicide-gene/drug combination is TK/GCV, the ability of the drug to kill tumor cells is limited by the stage of the cell cycle of the cells as GCV targets only cells in the process of DNA replication. It is thus unlikely that therapeutic gene delivery by these replication-defective vectors will affect tumor cells distant from the inoculation site, even in instances where the therapeutic gene produces a freely diffusible anticancer agent, such as cytokines or CPA metabolites.

Therefore, it remains of utmost importance to develop a safe and effective viral mutant for selectively killing neoplastic cells. Although various attempts have been made to engineer a viral mutant able to kill human tumor cells in vivo, presently no viral mutant combines the benefits of both viral and gene-therapy based approaches, thereby compensating for the limitations of each. There exists a need for a viral mutant that can both target neoplastic cells for viral mediated oncolysis and deliver a transgene capable of activating or enhancing a chemotherapeutic agent locally, wherein the transgene/chemotherapeutic agent combination does not significantly inhibit viral replication.

SUMMARY OF THE INVENTION

Accordingly, the present invention overcomes the disadvantages of the prior art by providing a viral mutant that can selectively target neoplastic cells for viral oncolysis and deliver a transgene encoding a product capable of activating or enhancing a chemotherapeutic agent, a method of using this viral mutant and a pharmaceutical composition containing this viral mutant.

In a preferred embodiment of the invention, the viral mutant comprises a (a) a mutation in a viral gene whose mammalian homologue is up-regulated in cells with elevated levels of E2F; and (b) an insertion into this viral gene, of a transgene encoding a gene product capable of converting a chemotherapeutic agent to its cytotoxic form, where the chemotherapeutic agent does not significantly inhibit replication of the viral mutant.

The invention also provides an embodiment of the foregoing viral mutant, wherein the viral mutant is derived from a herpes virus, particularly where the herpes virus is a herpes simplex virus, and more particularly, where it is herpes simplex virus type 1 or type 2.

In another embodiment, the viral gene, whose mammalian homologue is up-regulated in cells with elevated levels of E2F, encodes ribonucleotide reductase (RR), or more particularly the large subunit of RR. In an even more preferred embodiment, this viral gene encodes ICP6. Alternatively, the gene encoding RR encodes the small subunit.

In addition, the invention provides an embodiment of the foregoing viral mutant where the transgene encodes cytochrome P450. More particularly, this cytochrome P450 may be P450 2B 1, or alternatively P450 2B6, P450 2A6, P450 2C6, P450 2C8, P450 2C9, P450 2C11, or P450 3A4.

The invention also provides an embodiment of the foregoing viral mutant, & wherein the chemotherapeutic agent is a member of the oxazaphosphorine class, and particularly, where this agent is cyclophosphamide, or alternatively is ifosfamide, N-methyl cyclophosphamide, methylchloropropylnitrosourea, polymeric cyclophosphamide, polymeric ifosfamide, polymeric N-methyl cyclophosphamide, or polymeric methylchloropropylnitrosourea.

In a preferred embodiment of the invention, the viral mutant is derived from a herpes virus, and comprises: (a) a mutation in a gene encoding ribonucleotide reductase; and (b) an insertion into said gene, of a transgene encoding a cytochrome P450. In a particularly preferred embodiment of the invention, the viral mutant is derived from HSV-1, and the mutation comprises a deletion in the large subunit of the ribonucleotide reductase gene, especially in ICP6, and the cytochrome P450 encoded is P450 2B1. Alternatively, the cytochrome P450 encoded is P450 2B6, P450 2A6, P450 2C6, P450 2C8, P450 2C9, P450 2C11, or P450 3A4. In a particularly preferred embodiment of the foregoing viral mutant, the viral mutant is rRp450.

The present invention also provides a method for selectively killing neoplastic cells, using the viral mutant described above, comprising the steps of: (a) infecting the neoplastic cells with a viral mutant comprising: (i) a mutation in a viral gene whose mammalian homologue is up-regulated in cells with elevated levels of E2F, and (ii) inserted into said viral gene, a transgene encoding a gene product capable of converting a chemotherapeutic agent to its cytotoxic form, wherein said chemotherapeutic agent does not significantly inhibit replication of said viral mutant; (b) contacting the neoplastic cells with the chemotherapeutic agent; and (c) selectively killing the neoplastic cells.

In addition, the invention provides a method for selectively killing neoplastic cells comprising the steps of: (a) infecting neoplastic cells with a viral mutant comprising: (i)

a mutation in a gene encoding ribonucleotide reductase; and (ii) an insertion into this gene, of a transgene encoding a cytochrome P450; (b) contacting the neoplastic cells with a chemotherapeutic agent capable of being activated by the cytochrome P450; and (c) selectively killing the neoplastic cells. In a particularly preferred embodiment of this method, the viral mutant is derived from HSV-1, the mutation comprises a deletion in the large subunit of the ribonucleotide reductase gene, especially in ICP6, and the cytochrome P450 encoded is P450 2B 1. Alternatively, the cytochrome P450 encoded is P450 2B6, P450 2A6, P450 2C6, P450 2C8, P450 2C9, P450 2C11, or P450 3A4. In addition, the chemotherapeutic agent is preferably a member of the oxazaphosphorine class, particularly cyclophosphamide, ifosfamide, N-methyl cyclophosphamide, methylchloropropylnitrosourea, polymeric cyclophosphamide, polymeric ifosfamide, polymeric N-methyl cyclophosphamide, or polymeric methylchloropropylnitrosourea. In a particularly preferred embodiment of this method, the viral mutant is rRp450.

Another embodiment of the invention is a pharmaceutical composition containing the foregoing viral mutant, wherein this composition may also contain one or more pharmaceutically acceptable excipients.

Thus, the inventors have discovered that the combination of viral mediated oncolysis with activation, by the product of a transgene carried by the viral mutant, of a chemotherapeutic agent into metabolites that possess antineoplastic, but not antiviral-replication activity, provides a potentiated oncolytic effect much greater than that provided by either viral mediated oncolysis, or suicide gene therapy alone.

Other objects, features and advantages of the present invention will become apparent from the following detailed description. It should be understood, however, that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS

Figure 1A:
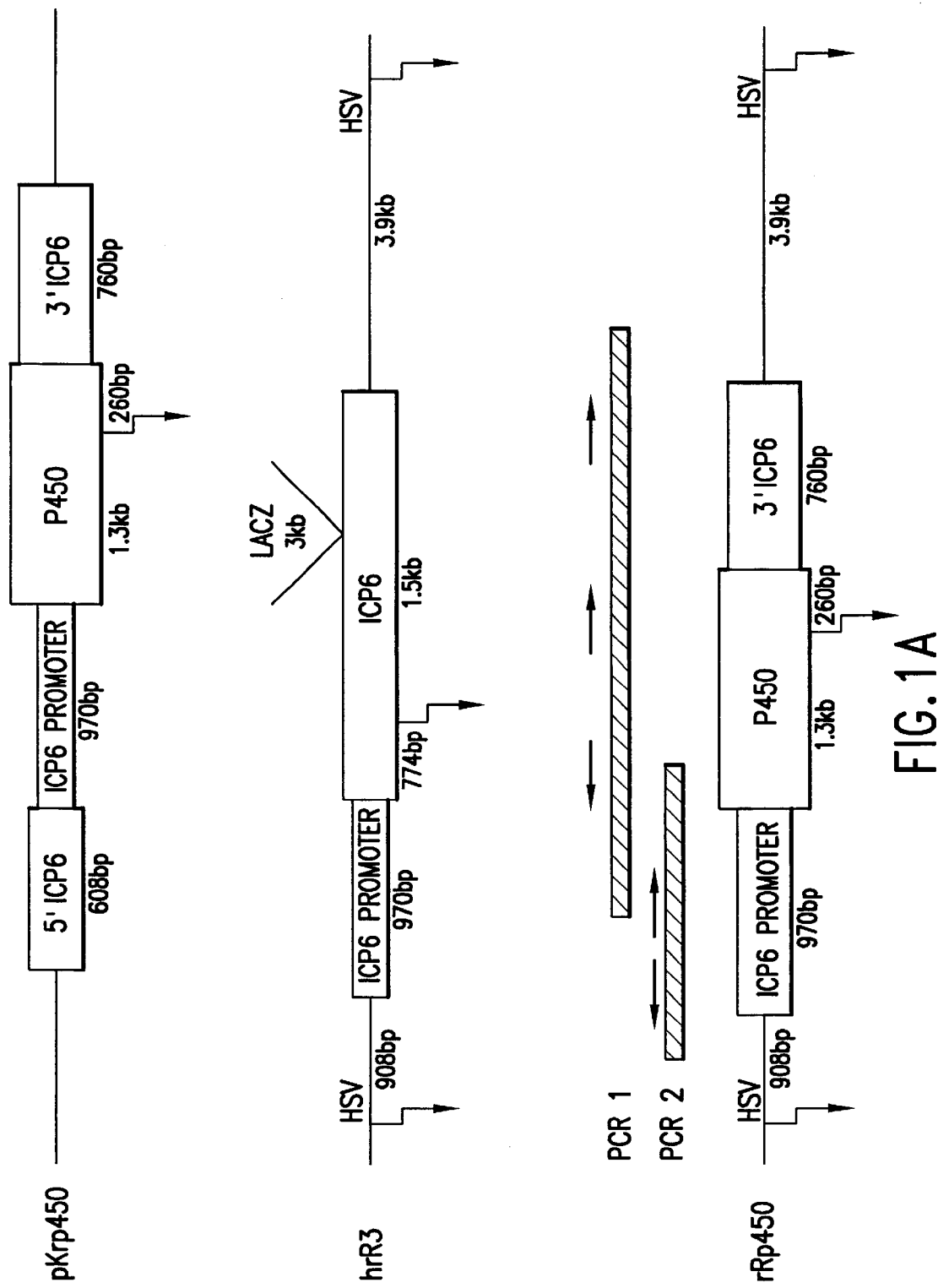
FIG. 1A depicts schematics of the linearized versions of plasmid pKrp450, the parent mutant herpes virus hrR3, and novel herpes recombinant rRp450. The jagged arrows at the bottom of each construct represent the location of the BsrDI restriction sites employed for the Southern blot analysis of DNA from hrR3 and rRp450. The approximate size of fragments is provided at the bottom. For rRp450, sequence analysis of two PCR fragments, amplified from infected cells, was performed. The two fragments are shown with labels PCR 1 and 2. The arrows above each fragment show the approximate location of the set of PCR primers used to sequence these two fragments. The abbreviations are as follows: bp stands for base pairs, kb stands for kilobases, and HSV stands for herpes simplex virus genome.

The present invention relates to the selective killing of neoplastic cells by combined viral mediated oncolysis and suicide gene therapy. The invention provides for a viral mutant, a method of killing neoplastic cells using this viral mutant, and a pharmaceutical composition containing the viral mutant. The viral mutant of the invention is capable of replicating in neoplastic cells, while sparing surrounding non-neoplastic tissue, and can deliver a transgene encoding a product that activates a chemotherapeutic agent. Thus, this viral mutant (i) targets neoplastic cells for death by viral replication, and (ii) provides a means of local activation of chemotherapeutic agents so that the cytotoxic forms of these agents act at tumor sites.

Design of the Viral Mutant

The viral mutants of the invention may be derived from several different types of viruses. By "derived from a virus" is meant that the virus is a source of viral DNA for making the viral mutant of the invention. Viruses that may be used to derive the viral mutants of the invention include herpes viruses, such as herpes simplex virus, cytomegalovirus, Epstein-Barr virus, varicella zoster virus, and psuedorabies virus. Other viruses that may be used to derive the viral mutants of the invention include members of the pox virus family, such as vaccinia virus and smallpox virus, or african swine fever virus.

Herpes simplex viruses are of particular interest. By "herpes simplex viruses" is intended any member of the subfamily *herpesviridae alpha* containing a mutation as described above. A preferred embodiment of the invention employs HSV-1 or HSV-2 to create the viral mutant, with HSV-1 being most preferred.

HSV-1 is a human neurotropic virus that is capable of infecting virtually all vertebrate cells. Natural infections follow either a lytic, replicative cycle or establish latency, usually in peripheral ganglia, where the DNA is maintained indefinitely in an episomal state. HSV-1 contains a double-stranded, linear DNA genome, 153 kilobases in length, which has been completely sequenced by McGeoch (McGeoch et al., *J. Gen. Virol.* 69: 1531 (1988); McGeoch et al., *Nucleic Acids Res* 14:1727(1986); McGeoch et al., J Mol. Biol. 181:1 (1985); Perry and McGeoch, *J Gen. Virol.* 69:2831 (1988)). DNA replication and virion assembly occurs in the nucleus of infected cells. Late in infection, concatemeric viral DNA is cleaved into genome length molecules which are packaged into virions. In the CNS, herpes simplex virus spreads transneuronally followed by intraaxonal transport to the nucleus, either retrograde or anterograde, where replication occurs.

The viral mutants of the invention possess a mutation in a gene required for replication, whose mammalian homologue is up-regulated by elevated levels of E2F. The viruses described above possess genes of this type. In a preferred embodiment of the invention, this gene is a ribonucleotide reductase gene.

Mammalian ribonucleotide reductase (mRR) is up-regulated during the $G_1$ phase of the cell cycle and its transcription is regulated by "free" E2F (DeGregori et al., *Mol. Cell. Biol.* 15:4215–4224 (1995); Lukas et al., *Mol. Cell. Biol.* 16: 1047–1057 (1996); Dynlacht et al., *Genes Dev.* 8: 1772–1786 (1994). It has been hypothesized that RR⁻ viral mutants selectively replicate in neoplastic cells owing to the presence of the complementing mammalian ribonucleotide reductase (mRR)) in these cells (Goldstein and Weller,*J. Virol.* 62: 196–205 (1988)). This has now been demonstrated in Example 2, below.

Elevation in the levels of free E2F causes increased expression of several mammalian genes whose viral homologues are required for replication of the virus. In addition to ribonucleotide reductase (rr), these genes include thymidine kinase (tk), uracil-DNA-glycosylase (ung), and uracil-triphosphatase enzymes (dUTPase). Viruses containing a mutation in one or more of these genes would replicate selectively in cells with elevated levels of free E2F. Thus, the invention encompasses viral mutants having a mutation in one or more of these genes.

E2F (including E2F1, E2F2, E2F3, E2F4, E2F5) appears to be the primary mediator of the cell cycle-regulated transcriptional cascade that involves p16, cyclin D/cdk4, and pRB ((DeGregori et al., *Mol. Cell. Biol.* 15: 4215–4224 (1995); Lukasetal., *Mol. Cell. Biol.* 16: 1047–1057(1996; Dynlachtetal., *Genes Dev.* 8: 1772–1786 (1994)). Thus, defects in a gene involved in this cascade can lead to increased levels of E2F and thereby increased levels of mammalian RR, TK, UNG and dUTPase. For example, cells with defects in the expression of p16, p21 and/or p27 may have increased levels of cyclin D, cyclin D kinase 4 (Cdk4) and/or cyclin D kinase 6 (Cdk6) which may in turn lead to increased phosphorylation of pRB thereby liberating E2F. In addition, cells with defects in the expression of pRB, p107 and or p130, DP1, DP2, and/or DP3 may also lead to increased liberation of E2F.

The majority of tumors possess an inactivation of a gene encoding a component of this cascade (Ueki et al., *Cancer Res.* 56: 150–153 (1996)), thus liberating E2F and allowing for transcription of mammalian rr, tk, ung, and dUTPase. Moreover, alterations in other tumor suppressor genes or oncogenes may also lead to increased levels of free E2F, and thereby increased levels of mammalian RR, TK, UNG and dUTPase. Therefore, RR⁻, TK⁻, UNG⁻ and dUTPase viral mutants may effectively target a large percentage of tumor cells, particularly if they possess a defect in the p16/cyclin D/pRB pathway that leads to an increase in "free" E2F.

Furthermore, tumor cells from many different origins (e.g., lung, breast, prostate, brain, liver, pancrease, skin, etc.) possess alterations in the pathways described above leading to elevated levels of RR, TK, UNG and dUTPase, and thus are targets for the viral mutant of the invention. For example, the tumor cell lines employed in the examples below (rat 9L, human U87, and human T98 cells) possess inactivating mutations of p16 (Van Meir et al., *Cancer Res.* 54: 649–652 (1994)), as well as elevated levels of mRR. These cells were thus able to complement the replication of the HSV-1 derived viral mutant rRp450 to levels close to that of the wild-type KOS strain, while neurons with no detectable level of mRR (and with a normal p16 pathway) did not.

By "ribonucleotide reductase gene" is intended a nucleic acid that encodes any subunit or part of the enzyme, ribonucleotide reductase, such that when this nucleic acid is expressed in a cell, this part or subunit is produced, whether functional or nonfunctional. Ribonucleotide reductase (RR) is a key enzyme in the de novo synthesis of DNA precursors, catalyzing the reduction of ribonucleotides to deoxyribonucleotides. HSV-1 encodes its own RR (UL39 and UL40 genes), which is composed of two non-identical subunits (Duita,*J. Gen. Virol.* 64: 513 (1983)). The large subunit (140 k molecular weight), designated ICP6, is tightly associated with the small subunit (38 k molecular weight). Herpes simplex virus RR has been found to be required for efficient viral growth in non-dividing cells but not in many dividing cells (Goldstein and Weller, *J. Virol.* 62: 196 (1988); Goldstein and Weller, *Virol.* 166: 41 (1988); Jacobson et al., *Virol* 173: 276 (1989)). Mutations in the small subunit of RR also lead to loss of RR activity and neuropathogenicity (Cameron et al., *J Gen. Virol.* 69: 2607 (1988)), however, particularly preferred are mutations in the large subunit.

The promoter region of ribonucleotide reductase ICP6 has been mapped to the 5' upstream sequences of the ICP6 structural gene (Goldstein and Weller, *J. Virol.* 62: 196 (1988); Sze and Herman, *Virus Res.* 26: 141 (1992)). The transcription start site for the small subunit of RR, namely UL40, falls within the coding region of ICP6 (McLauchlan and Clements,*J. Gen. Virol.* 64: 997 (1983); McGeoch et al., *J. Gen. Virol.* 69: 1531 (1988)).

Viral mutants derived from HSV-2 based on the viral mutants illustrated herein using the HSV-1 genome are encompassed by the present invention. HSV-2 contains both RR subunits; moreover, HSV-2 ICP10 is analogous to HSV-1 ICP6. Nikas et al., *Proteins* 1: 376 (1986); McLaughlan and Clements, *EMBO J.* 2: 1953 (1983); Swain and Halloway, *J. Virol.* 57: 802 (1986).

One difference between ribonucleotide reductase deficient (RR⁻) and other herpes simplex virus mutants is hypersensitivity to acyclovir and ganciclovir. Because TK⁻ HSV-1 mutants known in the art are resistant to these anti-viral agents, such mutants could be difficult to eliminate in the event of systemic infection or encephalitis. In contrast, in the event of viral encephalitis, TK⁺ viral mutants, such as RR⁻-HSV mutants, are responsive to antiviral therapy.

In addition, RR⁻-HSV mutants are compromised in their ability to produce infections and synthesize viral DNA at 39.5° C. in vitro. Goldstein and Weller, *Virology* 166: 41 (1988). Therefore, these mutants are attenuated for neurovirulence and less likely to propagate in the event of a fever in the infected host. Such characteristics are important to a therapeutic vector that must be of attenuated neurovirulence and amenable to antiviral therapy in the event of viral encephalitis.

The temperature sensitivity of RR⁻ viral mutants demonstrates another advantage of the viral mutant of the invention. In patients treated with a viral mutant, it is possible that a number of host factors (fever, antiviral immune responses) would inhibit propagation of the viral mutant. In these instances, it would be expected that treatment with the chemotherapeutic agent and activation by the transgene (for those cells infected by the viral mutant) would provide a supplemental anti-cancer treatment. The results disclosed in the examples below support this conclusion.

As used herein, "mutation" refers to any alteration to a gene wherein the expression of that gene is significantly decreased, or wherein the gene product is rendered nonfunctional, or its ability to function is significantly decreased. The term "gene" encompasses both the regions coding the gene product as well as regulatory regions for that gene, such as a promoter or enhancer. Such alterations render the product of the gene non-functional or reduce the expression of the gene such that the viral mutant has the properties of the instant invention. Moreover, the invention encompasses mutants with one or more mutation(s) in one or more gene(s) of interest. Thus, by "a" is intended one or more. For example, "a mutation in a ribonucleotide reductase gene" means that there can be one or more mutations in one or more ribonucleotide reductase genes.

Ways to achieve such alterations include (a) any method to disrupt the expression of the product of the gene or (b) any method to render the expressed ribonucleotide reductase nonfunctional. Numerous methods known to disrupt the expression of a gene are known, including the alterations of the coding region of the gene, or its promoter sequence in the by insertions, deletions and/or base changes. (See, Roizman and Jenkins, *Science* 229: 1208 (1985)).

A preferred mutation is the deletion of nucleic acids from a gene. A more preferred mutation is one wherein the mutation is produced by replacing a significant portion of a gene with a gene encoding a gene product capable of converting a chemotherapeutic agent to its cytotoxic form, wherein the chemotherapeutic agent does not significantly inhibit replication of the viral mutant. These genes are described further below.

Methods for the construction of engineered viruses and for the genetic manipulation of DNA sequences are known in the art. Generally, these include Ausubel et al., Chapter 16 in *Current Protocols in Molecular Biology* (John Wiley and Sons, Inc.); Paoletti et al., U.S. Pat. No. 4,603,112 (July 1986). Virological considerations also are reviewed in Coen, in *Virology*, 1990 ($2^{nd}$ ed.) Raven Press, pages 123–150.

The construction of HSV-1 mutants is described, for example, in Martuza et al., U.S. Pat. No. 5,585,096 (December 1996); Roizmann et al., U.S. Pat. No. 5,288, 641 (Febuary 1994); Roizman and Jenkins, *Science* 229:1208 (1985); Johnson et al., *J. Virol.* 66: 2952 (1992); Gage et al., *J. Virol.* 66: 5509 (1992); Spaete and Frenkel, *Cell* 30; 295 (1982); Goldstein and Weller, *J. Virol.* 62: 196 (1988), Coen, chapter 7, in *Virology*, 1990 ($2^{nd}$ ed.) Raven Press; Breakefield and DeLuca, *The New Biologist*, 3: 203 (1991); Leib and Olivo, *BioEssays* 15: 547 (1993); Glorioso et al., *Seminars in Virology* 3: 265 (1992); Chou and Roizman, *Proc. Natl. Acad. Sci. USA*, 89: 3266 (1992); Breakfield et al., *Molec. Neurobiol.* 1:339 (1987); Shih et al., in *Vaccines 85*, 1985, Cold Spring Harbor Press, pages 177–180,; Palella et al., *Molec. Cell. Biol.* 8: 457 (1988); Matz et al., *J. Gen. Virol.* 64: 2261 (1983); Mocarski et al., *Cell* 22: 243 (1980); and Coen et al., *Science* 234: 53 (1986).

Genetic alterations of the viral genome can be determined by standard methods such as Southern blot hybridization of restriction endonuclease digested viral DNA, sequencing of mutated regions of viral DNA, detection of new (or lost) restriction endonuclease sites, enzymatic assay for ribonucleotide reductase activity (Huszar and Bacchetti, *J. Virol.* 37: 580 (1981)). For cells lacking the mammalian homologue of the mutated viral gene, e.g., RR, genetic alteration of the viral genome can be determined by (1) Western blot or ELISA analysis of infected cell proteins with antibodies the viral homologue that has been mutated, e.g., RR, or (2) Northern blot analysis of infected cells for transcription of the viral homologue that has been mutated, e.g., RR (Jacobson et al., *Virology* 173: 276 (1989)). A viral mutant that has been mutated in one or more genes can be isolated after mutagenesis or constructed via recombination between the viral genome and genetically-engineered sequences.

By "up-regulated" is intended that expression of the gene(s) encoding the gene product said to be up-regulated is greater than the basal level of expression of this product as found in non-neoplastic cells.

By "level of free E2F is elevated" is meant that the amount of unbound E2F available in a cell is greater than the amount typically found in non-neoplastic cells.

By "selectively killing neoplastic cells" is meant that the viral mutant of the invention primarily targets neoplastic cells, rather than non-neoplastic cells. This targeting is due to having a mutation in a viral gene, wherein the viral gene is complemented by its mammalian homologue in mammalian cells in which levels of free E2F are elevated.

By "neoplastic cells" is meant cells whose normal growth control mechanisms are disrupted (typically by accumulated genetic mutations), thereby providing potential for uncontrolled proliferation. Thus, "neoplastic cells" can include both dividing and non-dividing cells. For purposes of the invention, neoplastic cells include cells of tumors, neoplasms, carcinomas, sarcomas, leukemias, lymphomas, and the like. Of particular interest are central nervous system tumors, especially brain tumors. These include glioblastomas, astrocytomas, oligodendrogliomas, meningiomas, neurofibromas, ependymomas, Schwannomas, neurofibrosarcomas, etc. The invention can be utilized to target for oncolysis both benign and malignant neoplastic cells in the periphery and the brain. As used herein, the term periphery is intended to mean all other parts of the body outside of the brain. Thus, a peripheral tumor is intended to mean a tumor in a part of the body outside of the brain.

The Transgene Carried by the Viral Mutant

In addition to having an altered gene, the viral mutants of the present invention carry a transgene that encodes a gene product capable of activating a chemotherapeutic agent to its cytotoxic form, wherein the activated chemotherapeutic agent does not significantly inhibit viral replication. This transgene may be inserted at any location in the viral genome where the transgene will be expressed, and where the insertion does not affect the ability of the virus to replicate in dividing cells. A preferred location for the transgene is in a gene required for viral replication, whose mammalian homologue is up-regulated by elevated levels of E2F, especially a ribonucleotide reductase gene. Even more preferred is insertion of the transgene into a ribonucleotide reductase gene containing a mutation.

In a preferred embodiment, the transgene is a cytochrome P450 gene. The term "gene encoding cytochrome P450" means a mammalian cytochrome P450 gene such as, P450 2B 1, P450 2B6, P450 2A6, P450 2C6, P450 2C8, P450 2C9, P450 2C 11, or P450 3A4. Each of these genes has been linked to activation of the anticancer drugs cyclophospharnide and ifosfamide (Clarke et al., *Cancer Res.* 49:2344–2350 (1989); Chang et al., *Cancer Res.* 53:5629–5637 (1993); Weber and Waxman, *Biochemical Pharmacology* 45:1685–1694 (1993)), and the cDNA sequences of these genes have also been published (Nelson et al., *DNA and Cell Biology* 12:1–51 (1993) and references cited therein; Yamano et al., *Biochem.* 29:1322–1329 (1990); Yamano et al., *Biochem.* 28:7340–7348 (1989)). Moreover, cytochrome P450 can also activate N-methyl cyclophosphamide (N-methyl CPA), methylchloropropylnitrosourea (MCPNU), and polymeric forms of CPA, ifosfamide, N-methyl CPA, and MCPNU. Polymeric forms of chemotherapeutic agents are discussed in Brem, *Biomaterials*, 11: 699–701 (1990); Buahin and Brem, *J. Neurooncol* 26: 103–110 (1995); Tamargo et al., *Cancer Res.* 53: 329–333 (1993); and Langer, *Ann. Biomed. Eng.* 23: 101–111 (1995). Persons of ordinary skill in the art should be able to utilize the method of the present invention with numerous other anticancer drugs that are activated by members of the cytochrome P450 family of enzymes (LeBlanc and Waxman, *Drug Metab. Rev.* 20:395–439 (1989)), as well as with drug-metabolizing cytochrome P450 genes from other species (e.g., mouse, rabbit, hamster, dog, etc.) that are homologous to cytochromes P450 2B1, P450 2B6, P450 2A6, P450 2C6, P450 2C8, P450 2C9, P450 2C 11, or P450 3A4, and whose cDNA sequences are known (Nelson et al., *DNA and Cell Biology* 12:1–51 (1993)). In a particularly preferred embodiment, the gene encoding cytochrome P450 2B1 is used.

Chemotherapeutic agents for use in the invention should not significantly inhibit replication of the viral mutant so as to allow the viral mutant to kill tumor cells by viral oncolysis, as well as by delivery of the suicide gene. The use of a chemotherapeutic agent/transgene combination in which the chemotherapeutic agent, or its active metabolites, act instead by crosslinking DNA or by inhibiting DNA repair would not significantly inhibit replication of the viral mutant. Thus, such chemotherapeutic agent/transgene combinations are encompassed by the viral mutant and methods of the present invention. A preferred chemotherapeutic agent/transgene combination is cytochrome P450 combined with CPA, ifosfamide, N-methyl cyclophosphamide, MCPNU, or polymeric forms of: CPA, ifosfamide, N-methyl cyclophosphamide and MCPNU. A more preferred chemotherapeutic agent/transgene combination is CPA/cytochrome P450 2B 1. Other chemotherapeutic agent/transgene combinations for use in the present invention include: CB1954/*E. coli* nitroreductase (Friedlos et al., *Gene Ther*. 5: 105–112 (1998); Green et aL, *Cancer Gene Ther*. 4: 229–238 (1997)); topoisomerase I or II inhibitors/enzyme with esterase-like activity, such as, e.g., CPT-11/carboxylesterase (Jansen et al., *Int. J. Cancer* 70. 335–340 (1997); Danks et al., *Cancer Res*. 58. 20–22 (1998)); 4-ipomeanol/cytochrome P450 4B1 (Verschoyle et al., *Toxicol. Appl. Pharmacol*. 123: 193–198 (1993)); and 2-aminoanthracene/cytochrome P450 4B1 (Smith et al., *Biochem. Pharmacol*. 50: 1567–1575 (1995)).

The results in the examples below demonstrate that the use of an alkylating agent such as CPA, while providing an anticancer effect, does not significantly inhibit viral protein synthesis or viral replication. The explanation for this finding may lie in the mode of action of these drugs. CPA's active metabolite, phosphoramide mustard (PM) produces interstrand and intrastrand crosslinks in cellular DNA. Maximum cytotoxicity to cellular DNA is usually achieved during mitosis when multiple DNA strand breaks occur at the cross-link sites (Colvin, in *Cancer Medicine*. eds. Holland et al., 1993. Lea and Fabiger, Philadelphia, pages 733–734). In contrast., non-mitotic, cross-linked viral DNA may be spared from extensive damage and may be thus be repaired more readily than cellular DNA.

Ganciclovir is one example of a chemotherapeutic agent that, when activated, inhibits viral replication. Although it has been demonstrated that the combination of hrR3 and ganciclovir provides a significant anticancer effect due to the conversion of ganciclovir by the viral thymidine kinase gene (Boviatsis et al., *Cancer Res*. 54: 5745–5751 (1994)), the converted ganciclovir molecules also inhibit viral replication. For this reason, use of TK/GCV may not be a preferred selection in this paradigm. Prodrug-activating enzymes, such as HSV-TK or *E. coli* cytosine deaminase, generate anticancer metabolites that act as "false" nucleotides, producing premature termination of replicating DNA strands. Therefore, these prodrug-activating enzymes would be expected to affect both viral and genomic DNA synthesis and would not be a good choice for use in the viral mutants of the invention.

Another advantage of using chemotherapeutic agents whose mechanism of action is the cross-linking of DNA or inhibition of DNA repair enzymes is that these agents are effective against even cells in $G_0$. Thus, for these agents to be effective in killing neoplastic cells, the targeted cells do not have to be actively dividing at the time that the drug is administered. This is a significant benefit for tumors in which a large percentage of cells are in $G_0$.

One example of this type of tumor is the glioblastoma. For glioblastomas, a the growth fraction, or the relative proportion of cells proliferating in the tumor at any one time, is only 30%, with the remaining 70% of cells being in $G_0$. These tumors are especially resistant to chemotherapeutic agents that target only actively dividing cells because, while the 30% of glioblastoma cells that are actively dividing contribute to the lethal progression of this tumor, 70% of the cells are in $G_0$ and may die or may re-enter the active cell cycle, Yoshii et al., *J. Neurosurg*. 65:659–663 (1986)). Thus, the 70% that are quiescent are responsible for the resistance of these tumors to chemotherapeutic agents that target actively proliferating cells.

This example demonstrates another advantage of the invention. The viral mutant and method of the present invention provide an advantage over therapies based on replication-conditional or replication-incompetent viral mediated oncolysis alone, in that those therapies will target only those cells that can complement the viral mutation. Whereas, although the viral mutant of the invention targets cells with elevated levels of E2F (primarily neoplastic cells) for replication in, and lysis, expression of the transgene and activation the chemotherapeutic agent provides active metabolites that can then diffuse to surrounding tumor cells. These metabolites can thereby kill even those surrounding tumor cells that do not have elevated levels of E2F, such as many cells in $G_0$ (70% of the cells in a glioblastoma).

The invention finds particular use in the treatment of glioblastomas. The glioblastoma represents approximately 30% or 50% of all primary brain tumors and, despite surgery, chemotherapy, and radiation therapy, is almost universally fatal. The mean survival is less than a year, and the five-year survival rate is only 3% or 5%. After treatment, recurrence of the disease often appears within two centimeters of the original site. Metastases are extremely rare; neurological dysfunction and death are due to local growth and cerebral invasion. Therefore, the possible efficacy of local (non-systemic) treatments has been explored. A few of these include studies of local hypothermia, photodynamic therapy, and interstitial radiation. However, until the present invention, no therapeutic modality has made a substantial impact on the outcome of patients with malignant gliomas.

Due to local activation of the chemotherapeutic agent by the gene product of the gene carried by the viral mutant, the method of the invention should allow more tumor toxicity at the same drug concentration, thus allowing for higher tumor doses without increasing toxicity to normal cells. Further, chemotherapeutic treatment of systemic tumor populations may also be improved by using the method of the present invention because lower doses of the drug may be possible by virtue of increased efficiency.

Furthermore, local activation of the chemotherapeutic agent provides another benefit. Some chemotherapeutic agents require activation or conversion to their active state in cells or organs in the periphery, however, often the active (cytotoxic) metabolites cannot cross the blood brain barrier, and thus are not effective against brain tumors. Thus, the method of the invention should allow treatment of brain tumors by these chemotherapeutic agents. One such chemotherapeutic agent is CPA. CPA is largely ineffective against central nervous system neoplasms as its conversion to DNA-alkylating, cytotoxic metabolites is restricted primarily to the liver and these metabolites do not readily cross the blood-brain barrier. However, the use of the viral mutant of the invention, engineered to carry a cytochrome P450 gene and applied to a brain tumor, would provide for local activation of CPA. Thus, in a preferred embodiment, a cytochrome P450 gene is utilized to sensitize central nervous tumor cells to the cytotoxic effects of cyclophosphamide (CPA).

By "gene product capable of converting a chemotherapeutic agent to its cytotoxic form" is meant a gene product that acts upon the chemotherapeutic agent to render it more cytotoxic than it was before the gene product acted upon it. Other proteins or factors may be required, in addition to this gene product, in order to convert the chemotherapeutic agent to its most cytotoxic form.

By "transgene encoding a gene product capable of converting a chemotherapeutic agent to its cytotoxic form" is meant a nucleic acid that upon expression provides this gene product.

"Cytotoxic" is used herein to mean causing or leading to cell death.

"Gene product" broadly refers to proteins encoded by the particular gene.

"Chemotherapeutic agent" refers to an agent that can be used in the treatment of neoplasms, and that is capable of being activated from a prodrug to a cytotoxic form. The chemotherapeutic agents for use in the invention do not significantly inhibit replication of the viral mutant, which means that viral replication can occur at a level sufficient to lead to death of the infected cell and to propagate the spread of the virus to other cells.

Administration of the Viral Mutant

Exemplary candidates for treatment according to the present invention include, but are not limited to (i) non-human animals suffering from neoplasms, (ii) humans suffering from neoplasms, (iii) animals suffering from nervous system tumors and (iv) patients having a malignant brain tumor, including astrocytoma, oligodendroglioma, meningioma, neurofibroma, glioblastoma, ependymoma, Schwannoma, neurofibrosarcoma, and medulloblastoma.

Preferentially, the treatment will be initiated by direct intraneoplastic inoculation. For tumors in the brain, MRI, CT, or other imaging guided stereotactic techniques may be used to direct viral inoculation, or virus will be inoculated at the time of craniotomy.

Generally, methods are known in the art for viral infection of the cells of interest. For example, the viral mutant can be injected into the host at or near the site of neoplastic growth, or administered by intravascular inoculation. Typically, the viral mutant would be prepared as an injectable, either as a liquid solution or a suspension; a solid form suitable for solution in, or suspension in, liquid prior to injection may also be prepared. The preparation also may be emulsified. The active ingredient is preferably mixed with an excipient which is pharmaceutically-acceptable and compatible with the active ingredient. Suitable excipients are, for example, water, saline, dextrose, glycerol, ethanol, or the like and combinations thereof. In addition, if desired, the preparation may contain minor amounts of auxiliary substances such as wetting or emulsifying agents, pH-buffering agents, adjuvants or immunopotentiators which enhance the effectiveness of the viral mutant (See *Remington's Pharmaceutical Sciences*, Gennaro, A. R. et al., eds., Mack Publishing Co., pub., 18th ed., 1990). Examples of non-aqueous solvents are propylene glycol, polyethylene glycol, vegetable oil and injectable organic esters such as ethyloleate. Aqueous carriers include water, aqueous solutions, saline solutions, parenteral vehicles such as sodium chloride, Ringer's dextrose, etc. Intravenous vehicles include fluid and nutrient replenishers. Determining the pH and exact concentration of the various components of the pharmaceutical composition is routine and within the knowledge of one of ordinary skill in the art (See *Goodman and Gilman's The Pharmacological Basis for Therapeutics*, Gilman, A. G. et al., eds., Pergamon Press, pub., 8th ed., 1990).

Additional formulations which are suitable include oral formulations. Oral formulations include such typical excipients as, for example, pharmaceutical grades of mannitol, lactose, starch, magnesium stearate, sodium saccharine, cellulose, magnesium carbonate and the like. Oral compositions may take the form of tablets, pills, capsules, sustained release formulations or powders and contain 10%–95% of active ingredient, preferably 25–70%.

The dosage of the viral mutant to be administered, in terms of number of treatments and amount, depends on the subject to be treated, the capacity of the subject's immune system to synthesize antibodies, and the degree of protection desired. Precise amounts of active ingredient required to be administered depend on the judgment of the practitioner and are peculiar to each individual. For the most part, the virus is provided in a therapeutically effective amount to infect and kill target cells.

The following examples are offered by way of illustration, not by way of limitation.

EXAMPLE 1

Example 1 demonstrates the genetic engineering of a viral mutant, rRp450, which was derived from a herpes virus, has a mutation in a ribonucleotide reductase gene, and carries a transgene encoding a cytochrome P450.

Methods and Materials

Generation of recombinant rRp450: In order to generate the rRp450 virus, a recombining plasmid (pkR450) was first engineered. This was accomplished by isolating gel purified fragments of: 1) the ICP6 (Hsrr) promoter (measuring approximately 970 nucleotides) from pD6p after digestion with BamHI and XhoI, and 2) the CYP2B1 gene (measuring approximately 1600 nucleotides) from pm450 after digestion with NcoI and EcoRi. An NcoI-XhoI adaptor was purchased from New England Biolabs, and a three-fragment ligation was performed into pBluescript KS, digested with BamHI and EcoRI. The resulting plasmid was thus designated as pBrR450. To generate the recombining plasmid, pBrR450 was linearized with EcoRI and then this site was blunt-ended with Klenow. After digestion with NcoI, the new NcoI-blunt fragment of CYP2B1 was gel-purified. The ICP6 (Hsrr) promoter was also gel purified by digesting pBrR450 with BamHI and NcoI. Finally, pKpX2 a plasmid containing the coding sequence of viral Hsrr (ICP6) was digested with BamHI and EcoRI. This removed a large portion of the ICP6 (Hsrr) sequence except for 608 nucleotides at the 5'- end and 760 nucleotides at the 3'- end. The EcoRI site was then blunt-ended with Klenow and gel-purified. A three fragment ligation was then performed using the NcoI-blunt CYP2B1 linearized DNA, the BamHI-NcoI ICP6 promoter linearized DNA, and the BamHI-blunt digested fragment of pKpX2. The new resulting plasmid was designated pKrp450 (FIG. 1A). The correct genetic identity of the plasmid was then confirmed by sequencing the nucleotides adjacent to the ligation junctions.

To engineer rRp450, viral DNA from hrR3 and pKrp450 viral DNA was co-transfected into Vero cells. Vero cell lysates were then freeze-thawed three times to release infectious virus and then replated onto Vero cells for three rounds of plaque purification of recombinant virus. Recombinant plaques were selected for loss of "blue" color. The initial screen yielded 36 plaques. After amplifying these plaques, 12 were analyzed by Southern blotting for presence of the CYP2B1 gene. Three of these appeared to possess an intact CYP2B1 gene. Viruses from these three plaques were thus purified through two additional rounds of plaque purification. One viral plaque was then selected for additional studies and virus from this plaque was designated as rRp450.

Figure 1B:
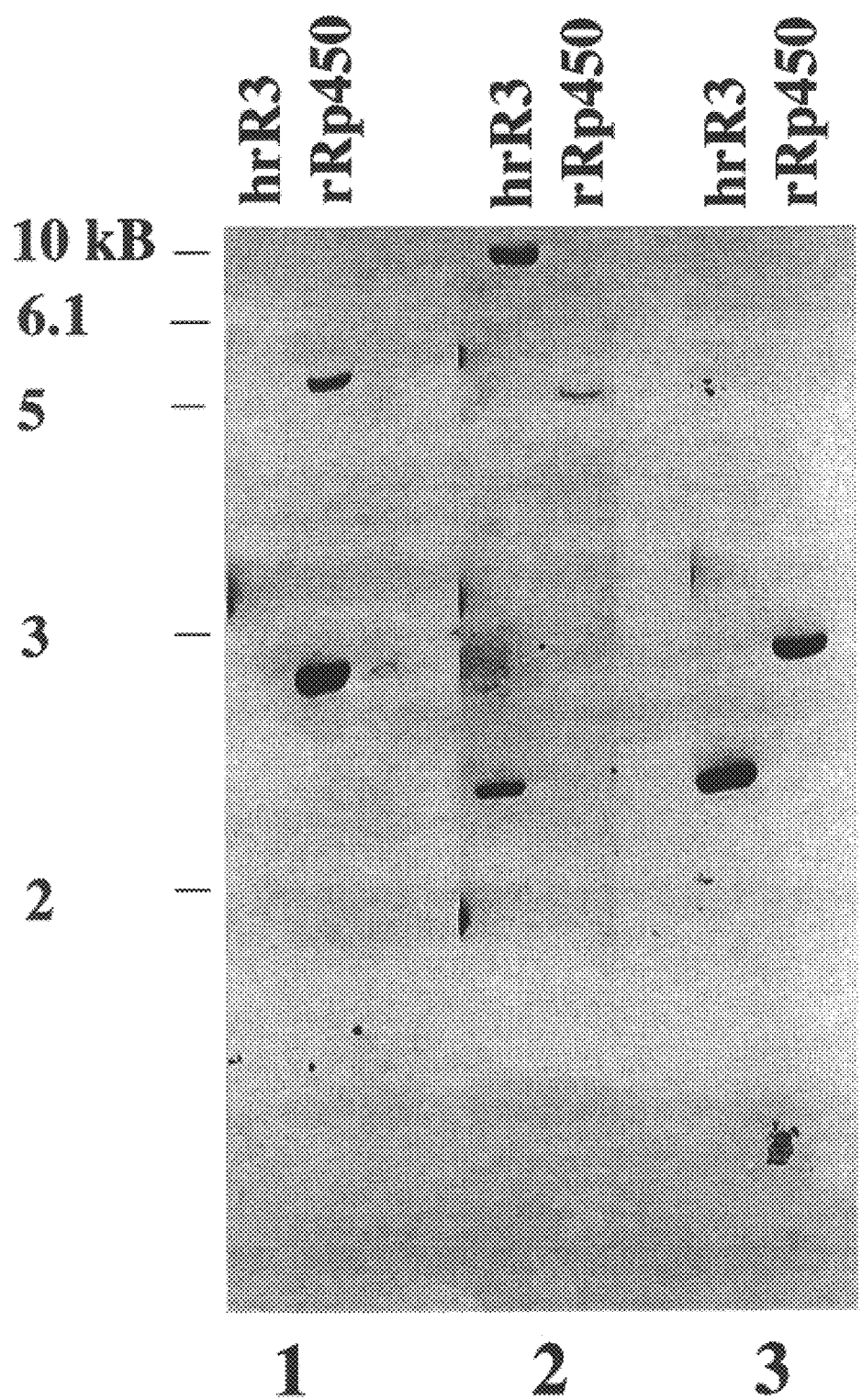
FIG. 1B is a photograph of the results of the Southern blot analyses of viral DNA purified from hrR3 and rRp450. The blot labeled 1 was hybridized with a full-length CYP2B1 probe. The blot labeled 2 was hybridized with a full-length Hsrr (ICP6) probe. The blot labeled 3 was hybridized with the 970 base pair ICP6 promoter probe. The approximate location of molecular weight markers is depicted to the left of the blots.

Southern blot analysis: Southern blot analysis was performed on hrR3 and rRp450 viral DNA digested with BsrDI (New England Biolabs) using a full length CYP2B1 probe and a full length ICP6 probe (FIG. 1B). After transfer to Hybond membranes (Amersham), hybridization was performed using a commercially available kit (Genius, Boehringer Mannheim), following the supplier's instructions.

DNA sequencing: In order to sequence viral DNA, two PCR fragments were generated: the first consisted of a 1200 nucleotide fragment obtained by hybridizing DNA from infected cells with primer 5'-ATGGTTCACACGC ACGTCTTC-3' (SEQ.ID.NO.1) (its complementary viral hybridizing sequence is located 190 nucleotides 5' to the ICP6 promoter recombining site) and with primer 5'-GGTCCTGGTGGGAAGTTGC-3' (SEQ. ID.NO.2) (its hybridizing sequence is located 80 nucleotides into the recombined CYP2B1 sequence; the second consisted of a 2900 nucleotide fragment obtained by hybridizing DNA from infected cells with primer 5'-TGTCACTCG TTGTTCGTTGAC-3' (SEQ.ID.NO.3) (its hybridizing sequence is located 540 nucleotides within the ICP6 promoter) and with primer 5'-GCGCCTGATTCGCCA CCTGGACG-3' (SEQ. ID. NO. 4) (its hybridizing sequence is located in the viral genome, 50 nucleotides 3' to the putative recombination site. The obtained sequence spanned the junction of parent viral DNA with recombining plasmid, as well as the junctions between the ICP6 promoter and the P450 gene and that between the P450 gene and the 3' region of ICP6. Partial sequence of these two fragments was obtained using two primers located in the ICP6 promoter region (5'-GAGCTGGCTCTTGATCAC-3' (SEQ. ID.NO.5) and 5'-TGTCACTCGTTGTTCGTTGAC-3') (SEQ.ID.NO. 3), two primers located in the P450 region (5'-GGTCC TGGTGGGAAGTTGC-3' (SEQ. ID.NO.2) and 5'-TCGCTGTGATTGAGCC-3' (SEQ.ID.NO.6)), and a primer located within the 3'-end of the Hsrr gene (5'-GCTTC GACGGGAGAGGATGCGG-3' (SEQ.ID.NO.7)). Sequence analysis was performed by the DNA sequencing core laboratory (Massachusetts General Hospital), verifying the correct identity of the recombined sites. PCR reactions were performed at an annealing temperature of 68° C. and an elongation time of three minutes. Reactions performed with DNA from cells infected with rRp450 using two different primers located within the 5'-region of Hsrr (ICP6) or with primers located within the lacZ region did not generate products. Primers were synthesized by a commercial source (Gibco BRL).

Plasmids and Viruses: pKpX2 (Goldstein and Weller, *J. Virol.* 62: 196–205 (1988)) is a plasmid that contains the full-length viral ICP6 gene (Hsrr) and was provided by Dr. S. Weller (University of Connecticut Medical School, Farmington, Conn.). The ICP6 promoter was generated by digesting pD6p (id.)(also provided by Dr. Weller) with BamHI and XhoI.

Plasmid pm450 (Wei et al., *Human Gene Therapy* 5: 969–978 (1994)) contains a full-length rat CYP2B1 transgene (Vallette et al., *Nucl. Acids. Red.* 17: 723–733 (1989)). The adenoviral vector bearing the CYP2B1 transgene was provided by Drs. Bruce Roberts, Rhonda Doll, and Alan Smith (Genzyme Corporation, Framingham, Mass.).

The hrR3 (provided by Dr. S Weller (University of Connecticut Medical School, Farmington, Conn.) ) viral mutant consists of an insertion of the lacZ gene into the viral ICP6 locus (Goldstein and Weller, *J. Virol.* 62. 196–205 (1988)). This generates a mutant that is defective in Hsrr function and that expresses a fusion ICP6-lacZ gene product. Viruses were routinely passaged on Vero cells (available from the American Type Culture Collection, Manassas, Va.) and maintained in stocks at −80 C.

Results

Genetic engineering of rRp450 was accomplished by "knocking-out" the lacZ gene from the parent virus, hrR3, with plasmid pKrp450 (FIG. 1A). The hrR3 mutant contains an *Escherichia coli* lacZ gene insertion in the ICP6 gene, which encodes the large subunit of ribonucleotide reductase. Viral DNA was analyzed by Southern blot analysis after digestion with BsrDI (FIG. 1B). The results of this analysis were consistent with a rRp450 genetic structure that contained a large deletion in the 5'-region of the viral Hsrr (ICP6) locus, lacked the lacZ gene, and possessed the CYP2B1 gene under control of the Hsrr (ICP6) promoter. As expected, the parent virus, hrR3, contained an insertion of lacZ within the intact Hsrr (ICP6) gene (Goldstein and Weller, *J. Virol.* 62: 196–205 (1988)). Southern blot analysis with a lacZ probe did not reveal hybridization to rRp450 DNA, but did show bands of expected molecular weight for hrR3. Sequence analysis confirmed the genetic structure, shown in FIG. 1A, for rRp450.

EXAMPLE 2

In Example 2, the oncolytic selectivity of rRp450 was analyzed by comparing viral replication and RR expression in normal cells to that in tumor cells.

Methods and Materials

Western analysis: Western blot analysis for mRR expression was performed on cell lysates from primary striatal neurons harvested from embryonic rats at day 18 of gestation, rat 9L gliosarcoma cells, and human U87 and T98 glioma cells. Cell lysates were resolved by electrophoresis in 10% SDS -polyacrylamide gels (20 ug of protein per lane), transferred to nitrocellulose and then probed with a commercially available mouse monoclonal antibody against human mRR (MAS 378 A0203, Accurate Chemical, Westbury, N.Y.). Equivalency of protein loading and transfer was verified by employing Ponceau S red staining of nitrocellulose membranes (BioRad). Detection of antigen-antibody reactions was performed using the ECL chemiluminescence system, following the supplier's instructions (Amersham).

Measurement of viral yields: Rat striatal neurons, rat 9L gliosarcoma, and human U87 glioma cells were infected with either wild-type HSV1 (strain KOS), rRp450 or d27 (an ICP 27 mutant of HSV that is replication-defective) (McCarthy et al., *J. Virol.* 63: 18–27 (1989)) at a MOI of 0.1 ($2\times10^5$ pfus was the input virus). Three days later, cells and supernatants were harvested. After releasing virus by freeze-thawing, plaque assays were performed on V27 cells (Vero cells stably transfected with ICP27).

Cell culture: Cells were usually plated the day before viral infection. The following day, 3 random dishes were trypsinized and cell numbers were enumerated using a Coulter counter. Based on the mean cell number, the viral mutant was added to achieve the desired multiplicity of infection (MOI). Experiments were performed in triplicate dishes.

To measure viral yields, cells and supernatants were harvested, freeze-thawed three times, and then added onto Vero cells. The additional step of sonification of cell pellets and supernatants did not appreciably alter the yield of virus. Plaques were counted using an agarose overlay, as described (Martuza et al., *Science* 252:854–856 (1991); Mineta et al., *Nature Med* 1:938–943 (1995); Boviatsisetal., *Cancer Res.* 54: 5745–5751 (1994); Kesari et al.,*Lab. Invest.* 73: 636–648 (1995); Chambers et al., *Proc. Natl. Acad. Sci. USA* 92: 1411–1415 (1995)).

Viruses: The wild-type HSV1 mutant virus (strain KOS) was provided by Dr. P. Schaffer (Harvard Medical School) but is also available from the American Type Culture Collection (Manassas, Va.). The d27 mutant virus and V27 cells were provided by Dr. David Knipe (Harvard Medical School)(See, Rice and Knipe,*J. Virol.* 64: 1704–1715 (1990).

Cell lines: Rat 9L gliosarcoma cells were provided by the Brain Tumor Research Laboratory (University of California at San Francisco Medical School). (See also, Weizsaecker et al., *J. Neurol.* 224: 183–197 (1981)). Vero cells and human U87 and T98 cells are available from the American Type Culture Collection (Manassas, Va.). Rat striatal neurons were provided By Dr. Francesca Persichetti (Molecular Neurogenetics Unit, Massachusetts General Hospital), who harvested them from the brains of embryonic rats on day 18 of gestation. Cell lines were maintained in culture in Dulbecco's minimal essential medium supplemented with 10% fetal calf serum, as well as 100 units of penicillin and 0.1 mg of streptomycin per ml of medium (Sigma). Incubations were carried out in an atmosphere of humidified 5% $CO_2$ at 37° C.

Results

Figure 2:
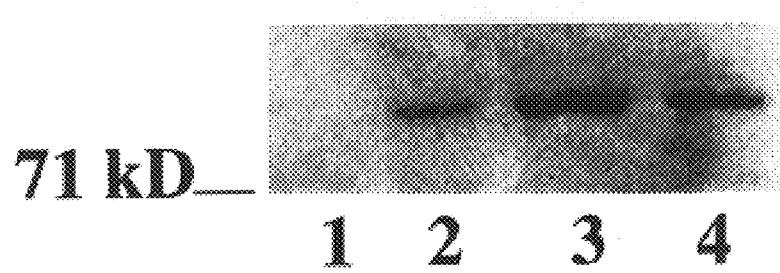
FIG. 2 depicts a western blot analysis performed using a monoclonal antibody against mRR. Lane 1 represents the cell lysate from neurons, lane 2 the lysate from rat 9L gliosarcoma cells, lane 3 the lysate from human U87 glioma cells, and lane 4 the lysate from human T98 cells. The size of a molecular weight marker is indicated on the left of the blot. The molecular weight of the immunoreactive band is approximately 90 kilodaltons.

The oncolytic selectivity of rRp450 was analyzed by comparing viral replication and RR expression in normal cells to tumor cells. Western blot analysis revealed that primary striatal neurons, did not express the mammalian ribonucleotide reductase (mRR) enzyme, while cultured tumor cells (9L, U87 and T98 cells) expressed elevated levels of the enzyme (FIG. 2). 9L and U87 cells were then infected in culture with rRp450, wild-type KOS virus, or d27, at low multiplicity of infection. Lysates from these cells were then plated onto V27 cells to determine viral yields. Table 1 shows that wild-type KOS virus replicated slightly better in rat 9L tumor cells compared to rat neurons. However, in rat neurons that do not express mRR, KOS replicated much better than rRp450 with an approximate difference of 3 logarithmic units. As expected, the replication of KOS and rRp450 achieved even higher yields of viral progeny in the human U87 tumor cell line. Control, replication-defective d27 virus did not produce viral progeny. These experiments thus indicated that rRp450 selectively replicated in tumor cells as compared to endogenous neurons and suggested that the increased viral yields were associated with up-regulation of Mrr.

TABLE I

Viral yields in infected cells[a]

| | Rat striatal neurons | Rat 9L glioma | Human U87 glioma |
|---|---|---|---|
| KOS | $3.8 \times 10^5$ | $5 \times 10^6$ | $3.1 \times 10^7$ |
| rRp450 | $4.3 \times 10^2$ | $8.3 \times 10^5$ | $1.2 \times 10^7$ |
| d27 | 0 | 0 | 0 |

[a]Rat striatal neurons, rat 9L gliosarcoma and human U87 glioma cells were infected with either wild-type HSV1 (strain KOS), rRp450 or d27 at a MOI of 0.1 ($2 \times 10^5$ pfus was the input virus). Three days later, cells and supernatants were harvested. After releasing virus by freeze-thawing, plaque assays were performed on V27 cells. Values represent the average number of plaque-forming units per ml of medium harvested from triplicate dishes.

EXAMPLE 3

In Example 3, delivery of the viral mutant to cells, and the level of expression of the transgene, CYP2B1, by infected cells, were evaluated.

Methods and Materials

Western blot analysis: Western blot analysis for CYP2B1 expression was performed on cell lysates from rat 9L gliosarcoma cells, and human T98G, U87, U343, and U138 glioma cells that had first been infected at an MOI=3 with vehicle, control hrR3 virus, or rRp450 virus for 16 hours. A polyclonal antiserum raised to rat CYP2B1 was used. As a control, western blot analysis using the polyclonal antiserum against CYP2B1 was also performed on cell lysate from C450-8 cells, a stably transfected rat C6 glioma cell line that expresses the CYP2B1 transgene.

Cell lysates were resolved by electrophoresis in 10% SDS-polyacrylamide gels (20 ug of protein per lane), transferred to nitrocellulose and then probed with the respective antibodies. Equivalency of protein loading and transfer was verified by employing Ponceau S red staining of nitrocellulose membranes (BioRad). Detection of antigen-antibody reactions was performed using the ECL chemiluminescence system, following the supplier's instructions (Amersham).

Cell culture: Cells were usually plated the day before viral infection. The following day, 3 random dishes were trypsinized and cell numbers were enumerated using a Coulter counter. Based on the mean cell number, the viral mutant was added to achieve the desired multiplicity of infection (MOI). Experiments were performed in triplicate dishes.

Antibodies: The polyclonal antibody against rat CYP2B1 was provided by Dr. David Waxman of Boston University (Waxman, D. J., *J. Biol. Chem.* 259: 15481–15490 (1984); Waxman, D. J., *J. Biol. Chem.* 257: 10446–10457 (1982)).

Viruses: The hrR3 viral mutant (provided by Dr. S Weller (University of Connecticut Medical School, Farmington, Conn.)) consists of an insertion of the lacZ gene into the viral ICP6 locus (Goldstein and Weller,*J. Virol.* 62. 196–205 (1988). This generates a mutant that is defective in Hsrr function and that expressesa fusion ICP6-lacZ gene product.

Cell lines: Rat 9L gliosarcoma cells were provided by the Brain Tumor Research Laboratory (University of California at San Francisco Medical School) (See also, Weizsaecker et al., *J. Neurol.* 224: 183–197 (1981)). Human U87, T98, U343, and U138 cells were obtained from the American Type Culture Collection, (Manassas, Va.). Cell lines were maintained in culture in Dulbecco's minimal essential medium supplemented with 10% fetal calf serum, as well as 100 units of penicillin and 0.1 mg of streptomycin per ml of medium (Sigma). Incubations were carried out in an atmosphere of humified 5% $CO_2$ at 37° C.

Results

Figure 3:
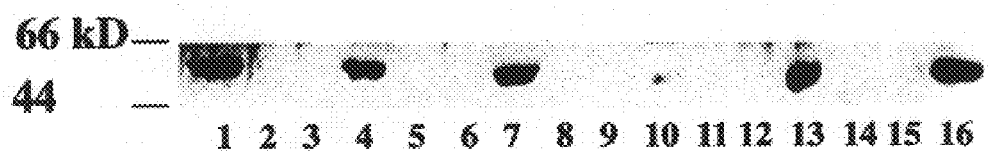
FIG. 3 depicts western blots performed using a polyclonal antibody raised against rat CYP2B1. Lane 1 represents C450-8 cells, a rat C6 glioma cell line that is stably transfected with the CYP2B1 transgene. Rat 9L gliosarcoma (lanes 2–4), human T98G (lanes 5–7), human U87 (lanes 8–10), human U343 (lanes 11–13), and human U138 (lanes 14–16) glioma cells were infected with mock (lanes 2,5,8, 11,14), hrR3 mutant (lanes 3,6,9,12,15), or rRp450 (lanes 4,7,10,13,16). The sizes of molecular weight markers is indicated on the left side of the blot.

To test the delivery and expression of the transgene, the expression of the CYP2B1 gene by virally-infected cells was measured. Rat 9L gliosarcoma cells and human T98G, U87, U343, and U138 glioma cells were infected with vehicle, control hrR3 virus, or rRp450 virus. Western blot analysis of infected cell lysates was carried out using a polyclonal antibody raised against rat CYP2B1. Tumor cells infected with rRp450 expressed the CYP2B1 gene, while cells infected with the parent virus, hrR3, or control cells did not (FIG. 3). As a control, C450-8 cells, a stably transfected rat C6 glioma cell line that expresses the CYP2B1 transgene, were included in the analysis. These results thus indicated that the oncolytic viral mutant delivered and expressed the foreign transgene in tumor cells.

EXAMPLE 4

In Example 4, the effect of cyclophosphamide and its activated metabolites on viral replication was evaluated.

Methods and Materials

Measurement of Viral Protein Synthesis: 9L tumor cells were grown in the presence of 250 uM CPA, 100 ng/ml ganciclovir, or vehicle for 30 hours. Cells from each group were then infected with rRp450 or hrR3 at an MOI=3. Control plates were infected with a mock viral preparation. Eighteen hours later, medium was removed and fresh medium containing 20 uCi of $^{35}$S-methionine was added. Cells were then scraped and harvested two hours later. Cell pellets were resuspended in sodium phosphate, pH=7.3. in 0.9% sodium chloride in the presence of protease inhibitors and then sheared by passage through a 28 and a ½ gauge needle. Protein concentrations were calculated by using a commercially available kit (BioRad). Proteins were then separated using a 10% SDS-polyacrylamide gel (30 ug of protein per lane). After drying the gel, autoradiography was performed.

Measurement of Viral Yields:9L cells (3×105 cells plated on a 6 cm dish) were infected with rRp450 or hrR3 (as a control) at a MOI of 0.1 in the presence of cyclophosphamide (250 uM) or vehicle. Three day later, cells and supernatants were harvested and virus was harvested by freeze-thawing three times. Plaque-assays on Vero cells were performed to measure viral yields. Assay was performed in triplicate plates. The additional step of sonication of cell pellets and supernatants did not appreciably alter the yield of virus. Plaques were counted using an agarose overlay, as described (Martuza et al., Science 252:854–856 (1991); Mineta et al., Nature Med 1:938–943 (1995); Boviatsis et al., Cancer Res. 54: 5745–5751 (1994); Kesari et al., Lab. Invest. 73: 636–648 (1995); Chambers et al., Proc. Natl. Acad. Sci. USA 92: 1411–1415 (1995)).

Cell culture studies: Cells were usually plated the day before viral infection. The following day, 3 random dishes were trypsinized and cell numbers were enumerated using a Coulter counter. Based on the mean cell number, the viral mutant was added to achieve the desired multiplicity of infection (MOI). Experiments were performed in triplicate dishes.

CPA: CPA was added at the start of the incubation period at a concentration of 250 Um.

Viruses: The hrR3 viral mutant (provided by Dr. S Weller (University of Connecticut Medical School, Farmington, Conn.)) consists of an insertion of the lacZ gene into the viral ICP6 locus (Goldstein and Weller, J. Virol. 62: 196–205 (1988). This generates a mutant that is defective in Hsrr function and that expresses a fusion ICP6-lacZ gene product.

Cell lines: Rat 9L gliosarcoma cells were provided by the Brain Tumor Research Laboratory (University of California at San Francisco Medical School)(See also, Weizsaecker et al., J. Neurol. 224: 183–197(1981)). Vero cells are available from the American Type Culture Collection (Manassas, Va.). Cell lines were maintained in culture in Dulbecco's minimal essential medium supplemented with 10% fetal calf serum, as well as 100 units of penicillin and 0.1 mg of streptomycin per ml of medium (Sigma). Incubations were carried out in an atmosphere of humified 5% $CO_2$ at 37° C.

Results

Figure 4:
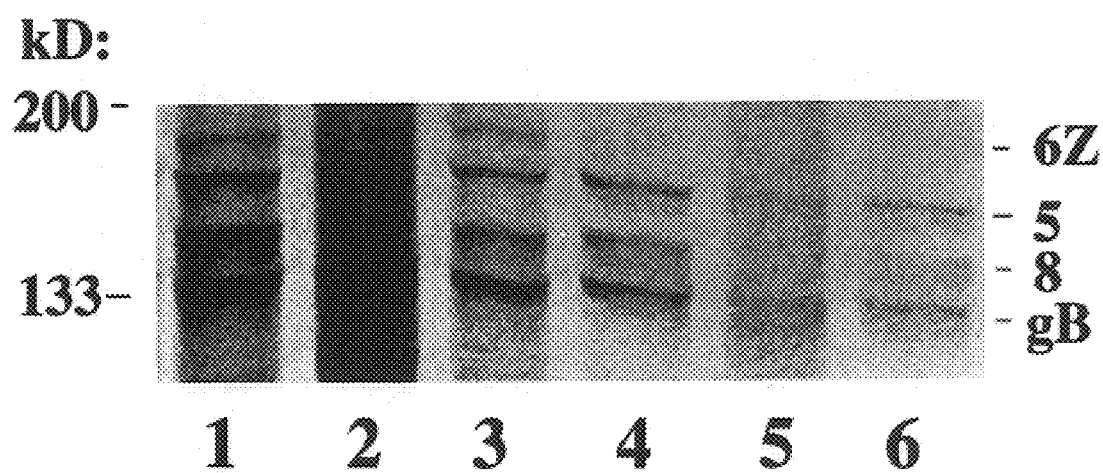
FIG. 4 is an autoradiograph depicting the effect of CPA on rRp450 protein synthesis in infected 9L tumor cells. 9L tumor cells were grown in the presence of CPA (lanes 3 and 6), 100 ng/ml ganciclovir (lanes 2 and 5), or vehicle (lanes 1 and 4). Cells from each group were then infected with rRp450 (lanes 4–6) or hrR3 (lanes 1–3). After pulsing with $^{35}$S-methionine, cell lysates were separated by electrophoresis. The designations, 6,5,8, gB, and pgB indicate the viral ICP6-lacZ fusion, ICP5, ICP8, and glycoprotein B, respectively. The size of molecular weight markers is indicated on the left side of the blot.

Since addition of the prodrug, cyclophosphamide, to infected cells might decrease viral titers by alkylation of freshly synthesized viral DNA by cyclophosphamide's active metabolites, 9L cells were pulsed with [$^{35}$S]-methionine 18 hours after infection with rRp450 or hrR3 in the presence of ganciclovir (an inhibitor of viral DNA synthesis that is activated by the viral thymidine kinase enzyme), or in the presence of cyclophosphamide. FIG. 4 shows that ganciclovir inhibited the synthesis of viral proteins in both rRp450-(lane 6) and hrR3-infected (lane 3) cells, as expected. This was most evident with the disappearance of a set of high molecular weight infected cell polypeptides (ICP) representing the ICP6-lacZ fusion protein (lanes 1–3 only), ICP5, ICP8, and gB (McCarthy et al., J. Virol. 63: 18–27 (1989)). However, cyclophosphamide did not appear to significantly inhibit viral protein synthesis in either rRp450-(lane 6) or hrR3-infected (lane 3) 9L cells. Interestingly, in hrR3-infected cells, an ICP6-lacZ fusion protein is synthesized (Goldstein and Weller, J. Virol. 62: 196–205 (1988)), while there is no visible synthesis of ICP6 sequences in the rRp450-infected tumor cells. These results thus indicated that CPA metabolites activated by rRp450 within infected tumor cells did not significantly inhibit viral protein synthesis.

To further confirm the hypothesis that activated CPA did not inhibit replication of rRp450 virus, 9L cells were infected with rRp450 in the presence or absence of cyclophosphamide. Three days later, cells and supernatants were harvested and viral yields were determined. Table II demonstrates that CPA did not significantly inhibit replication of rRp450. Furthermore, CPA, at concentrations up to 200 uM, did not inhibit plaque production on a confluent, contact-inhibited monolayer of Vero cells, while ganciclovir did. Taken in conjunction, these results indicated that expression of CYP2B1 in infected tumor cells did not significantly inhibit viral protein synthesis and progeny production.

TABLE II

Viral yields from infected 9L cells treated with cyclophosphamide[a]

|  | Saline | Cyclophosphamide |
| --- | --- | --- |
| hrR3 | 1.3 (+/− 0.2) × 10$^5$ pfus[b] | 7.5 (+/− 2.5) × 10$^4$ pfus |
| rRp450 | 5 (+/− 1.4) × 10$^4$ pfus | 6.7 (+/− 2.2) × 10$^4$ pfus |

[a]9L cells (3 × 10$^5$ cells plated on a 6 cm dish) were infected with rRp450 or hrR3 (as a control) at a MOI of 0.1 in the presence of cyclophosphamide (250 uM) or vehicle. Three day later, cell and supernatants were harvested and virus was harvested by freeze-thawing. Plaque-assays on Vero cells were performed to measure viral yields. Values in parenthesis represent the standard error. The assay was performed in triplicate plates.
[b]plaque-forming units.

EXAMPLE 5

In the next experiment, the oncolytic effect provided by viral replication plus converted CPA metabolites, or by CPA metabolites alone after viral inactivation, were evaluated.

Methods and Materials

To test the combined oncolytic effect on tumor cells of rRp450 plus CPA, $3 \times 10^5$ 9L tumor cells were plated onto 6 cm dishes. After 6 hours, cells were washed and either hR3 or rRp450 was added at an MOI=0.5 together with is vehicle or 250 uM CPA. Five days later, surviving cells were counted.

Next the oncolytic effect of rRp450 plus CPA where viral replication of rRp450 was temperature inactivated was tested. $3 \times 10^5$ 9L tumor cells were plated onto 6 cm dishes. After 6 hours, cells were washed and either hR3 or rRp450 were added at an MOI=1 in the presence of vehicle or CPA. Viral replication was attenuated 14 hours later by raising the temperature of the incubator to 39.5° C. Incubation at 37° C. was continued for control dishes. Five days later, surviving cells were counted.

Cell culture: Cells were usually plated the day before viral infection. The following day, 3 random dishes were trypsinized and cell numbers were enumerated using a Coulter counter. Based on the mean cell number, the viral mutant was added to achieve the desired multiplicity of infection (MOI). Experiments were performed in triplicate dishes.

CPA: CPA was added at the start of the incubation period at a concentration of 250 uM. To measure effects on cellular proliferation, cells were washed three times with Hanks' buffered saline (HBS) to remove dead, unattached cells prior to enumeration in a Coulter counter.

Viruses: The hrR3 viral mutant (provided by Dr. S Weller (University of Connecticut Medical School, Farmington, Conn.)) consists of an insertion of the lacZ gene into the viral ICP6 locus (Goldstein and Weller, *J. Virol.* 62: 196–205 (1988). This generates a mutant that is defective in Hsrr function and that expresses a fusion ICP6-lacZ gene product.

Cell lines: Rat 9L gliosarcoma cells were provided by the Brain Tumor Research Laboratory (University of California at San Francisco Medical School)(See also, Weizsaecker et al., *J. Neurol.* 224: 183–197 (1981)). Vero cells are available from the American Type Culture Collection (Manassas, Va.). Cell lines were maintained in culture in Dulbecco's minimal essential medium supplemented with 10% fetal calf serum, as well as 100 units of penicillin and 0.1 mg of streptomycin per ml of medium (Sigma). Incubations were carried out in an atmosphere of humified 5% $CO_2$ at 37° C.

Results

Figure 5A:
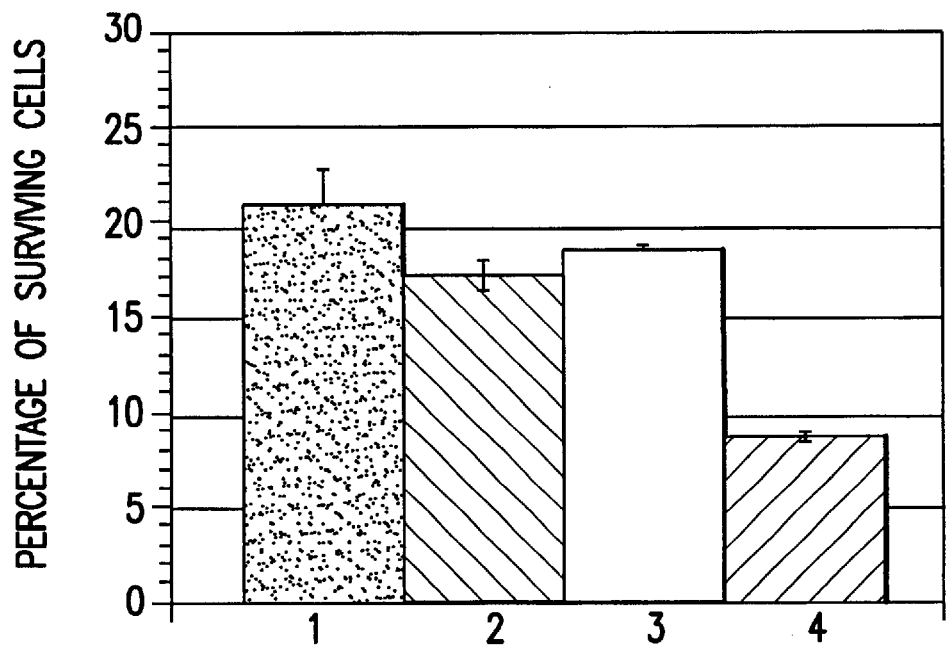
FIG. 5A is a bar graph depicting the combined oncolytic effect on tumor cells of rRp450 plus CPA. Cells were exposed to virus plus prodrug (or saline) for the duration of the experiment. Bar 1 represents the percentage of surviving 9L cells after treatment with hrR3 plus vehicle, bar 2 represents the percentage of surviving 9L cells after treatment with hrR3 plus CPA, bar 3 represents the percentage of surviving 9L cells after treatment with rRp450 plus vehicle, and bar 4 represents the percentage of surviving cells after treatment with rRp450 plus CPA. Differences between group D and other treatment groups were significant ($P<0.001$, one way analysis of variance with Bonferroni t-test method). Reported percentages represent the average from triplicate dishes and error bars represent the standard error of the mean. Percentages were determined by using the number of control 9L cells, grown in parallel for the 6-day experimental period, as the denominator.
Figure 5B:
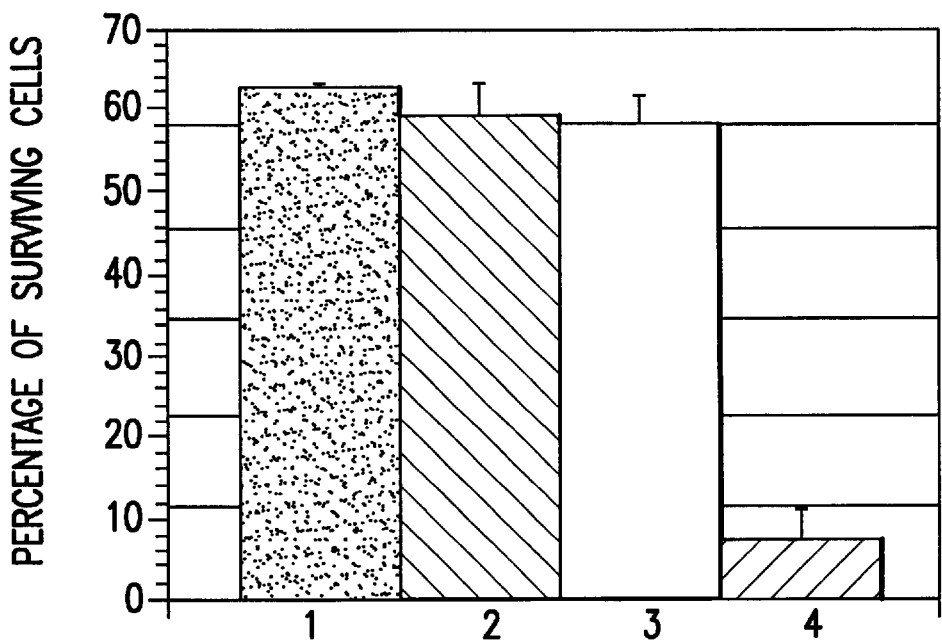
FIG. 5B is a bar graph depicting the oncolytic effect of rRp450 plus CPA where viral replication of rRp450 was temperature inactivated. Cells were exposed to prodrug (or saline) and virus that was inactivated after one cycle of replication. Bar 1 represents the percentage of surviving 9L cells after treatment with hrR3 plus vehicle, bar 2 represents the percentage of surviving 9L cells after treatment with hrR3 plus CPA, bar 3 represents the percentage of surviving 9L cells after treatment with rRp450 plus vehicle, and bar 4 represents the percentage of surviving cells after treatment with rRp450 plus CPA. Differences between group D and other treatment groups were significant ($P<0.001$, one way analysis of variance with Bonferroni t-test method). Reported percentages represent the average from triplicate dishes and error bars represent the standard error of the mean. Percentages were determined by using the number of control 9L cells, grown in parallel for the 6-day experimental period, as the denominator.

To determine whether tumor cells infected with rRp450 exhibited less viability in the presence of CPA, a proliferation assay was performed. Rat 9L gliosarcoma cells were infected with either hrR3 or rRp450 in the presence of CPA or vehicle. Five days later, cells were counted. FIG. 5A shows that there was an approximate 10% increase in 9L cell killing after infection with rRp450 in the presence of CPA compared to infection with rRp450 in the presence of vehicle. Since the oncolytic effect in this experiment is provided by both viral replication and converted CPA metabolites, this experiment provided a means to better characterize the effect of the latter. It has been reported that Hsrr mutants of HSV-1 are severely impaired in their ability to replicate at elevated temperatures (Mineta et al., *Cancer Res.* 54: 3936–3966 (1994)). 9L cells were thus infected with hrR3 or rRp450 in the presence of CPA or vehicle for 14 hours and then viral replication was inactivated by raising the temperature from 37° C. to 39.5° C. Six days later, surviving cells were counted. FIG. 5B shows that less than 10% of 9L cells survived treatment with CPA and a 14-hour pulse of active rRp450 (bar 4), while 60% of cells survived treatment with a 14-hour pulse of active hrR3 in the presence of saline (bar 1) or CPA (bar 2) or with a 14-hour pulse of rRp450 of active rRp450 in the presence of saline (bar 3). Taken in conjunction, these results indicated that rRp450 was indeed able to activate CPA in infected cells and that activated CPA metabolites significantly augmented the viral oncolytic effect.

EXAMPLE 6

In Example 6, the in vivo augmentation by CPA of the viral mutant's oncolytic effect was evaluated.

Methods and Materials 9L tumors were established as visible subcutaneous nodules (the range of volumes was 10–135 $mm^3$ and the average volume was 74 $mm^3$) by the injection of $10^5$ rat 9L gliosarcoma cells into the flanks of athymic mice (NCY/sed, nu/nu; MGH breeding colony). Fifteen days later, visible tumors were treated with intratumoral injections, using a Hamilton syringe, of rRp450 ($2.5 \times 10^8$ pfus) plus vehicle in 125 ul of medium, or rRp450 ($2.5 \times 10^8$ pfus) plus 2 mg CPA in 125 ul of medium. Control tumors were treated with control, heat-inactivated virus. Heat inactivation of rRp450 was performed by boiling the virus for 10 minutes and confirming its inactivation by failure to form plaques on Vero cells. Control adenovirus-P450 ($2.5 \times 10^8$ pfu/ml) was also inoculated in the presence of 1 mg of CPA in a total of 125 ul of medium. Tumor inoculations were repeated on day 2, day 4 and day 6. Five mice were used per treatment group. Volume measurements were obtained at 1,7,11, 16,19 and 23 days using external calipers (Martuza et al., *Science* 252:854–856 (1991); Mineta et al., *Nature Med* 1:938–943 (1995); Boviatsis et al., *Cancer Res.* 54: 5745–5751 (1994)).

Animals were euthanized on day 29. A 1 mm piece of tumor was removed from animals of each group and placed in 1 ml of medium for 1–2 minutes. The medium was then added onto Vero cells to measure ongoing viral replication in tumor samples.

In a similar experiment, visible subcutaneous nodules (the range of volumes was 10–135 $mm^3$ and the average volume was 74 $mm^3$) were established by the injection of $10^6$ human U87 glioma cells into the subcutaneous flank of athymic mice (NCY/sed, nu/nu; MGH breeding colony). Thirty days later the tumors were treated with intratumoral injections, using a Hamilton syringe, of 1 mg CPA in 125 ul of medium, rRp450 ($2.5 \times 10^8$ pfus) plus vehicle in 125 ul of medium, or rRp450 ($2.5 \times 10^8$ pfus) plus 1 mg CPA in 125 ul of medium. Tumor inoculations were repeated on day 2, day 4 and day 6. Five mice were used per treatment group. Volume measurements were obtained at 1, 7, 11, 15, 18, 22, 26 and 29 days using external calipers (Martuza et al., *Science* 252:854–856 (1991); Mineta et al., *Nature Med* 1:938–943 (1995); Boviatsis et al., *Cancer Res.* 54: 5745–5751 (1994)).

Animals were euthanized on day 29. A 1 mm piece of tumor was removed from animals of each group and placed in 1 ml of medium for 1–2 minutes. The medium was then added onto Vero cells to measure ongoing viral replication in tumor samples.

To compare the in vivo oncolytic effect on tumors of rRp450 plus CPA to the in vivo oncolytic effect on tumors of replication defective virus plus CPA, U87 tumors were established by the injection of $1\times10^5$ human U87 glioma cells into the subcutaneous flank of athymic mice (NCY/sed, nu/nu; MGH breeding colony, 5 mice per group). Thirty days later these tumors were treated with intratumoral injections, using a Hamilton syringe, of 1 mg of CPA plus rRp450 ($2.5\times10^8$ pfus) in 125 ul of medium, or 1 mg CPA plus a replication-defective vector consisting of an E1 deleted adenoviral vector bearing the CYP2B1 transgene ($2.5\times10^8$ pfu/ml) in 125 ul medium. Tumor inoculations were repeated on day 2, day 4 and day 6. Volume measurements were obtained at 1, 7, 14, and 21 days using external calipers (Martuza et al., Science 252:854–856 (1991); Mineta et al., Nature Med 1:938–943 (1995); Boviatsis et al., Cancer Res. 54: 5745–5751 (1994)).

Animals were euthanized on day 29. A 1 mm piece of tumor was removed from animals of each group and placed in 1 ml of medium for 1–2 minutes. The medium was then added onto Vero cells to measure ongoing viral replication in tumor samples.

Animal studies: Animal studies were performed in accordance with guidelines issued by the Massachusetts General Hospital Subcommittee on Animal Care. Viral inoculation and care of animals harboring viruses were performed in approved viral vector rooms.

Viruses: The hrR3 viral mutant (provided by Dr. S Weller (University of Connecticut Medical School, Farmington, Conn.)) consists of an insertion of the lacZ gene into the viral ICP6 locus (Goldstein and Weller, J. Virol. 62: 196–205 (1988)). This generates a mutant that is defective in Hsrr function and that expresses a fusion ICP6-lacZ gene product.

Cell lines: Rat 9L gliosarcoma cells were provided by the Brain Tumor Research Laboratory (University of California at San Francisco Medical School)(See also, Weizsaecker et al., J. Neurol. 224: 183–197(1981)). Vero cells and human U87 cells are available from the American Type Culture Collection (Manassas, Va.). Cell lines were maintained in culture in Dulbecco's minimal essential medium supplemented with 10% fetal calf serum, as well as 100 units of penicillin and 0.1 mg of streptomycin per ml of medium (Sigma).

Results

Figure 6A:
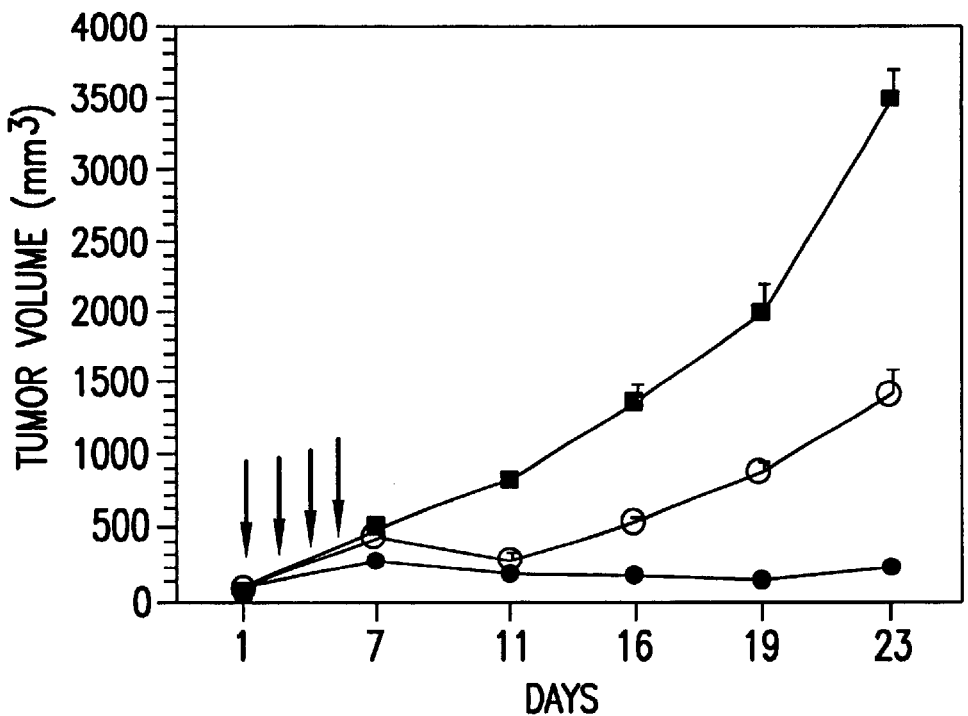
FIG. 6A is a graph depicting the in vivo augmentation of rRp450's oncolytic effect by CPA on 9L tumors. Rat 9L tumors were inoculated with rRp450 plus vehicle (open circles), rRp450 plus CPA (closed circles), or heat-inactivated rRp450 (closed squares). The black vertical arrows indicate the times of injection (days 1, 2, 4, and 6). Values represent the average tumor volume from 5 mice per group. Error bars represent the standard error of the mean. For this experiment, differences in tumor volumes were statistically significant at the 16, 19, and 23 day time point ($P<0.05$, One way analysis of variance).

The ability to use a viral mutant to selectively lyse tumor cells as well as to deliver a prodrug-activating gene, such as CYP2B1, whose action does not inhibit viral replication, could offer a therapeutic advantage in anticancer therapy. To test this hypothesis, rat 9L tumors were established in the subcutaneous flank of athymic mice and injected with rRp450 plus vehicle, or rRp450 plus CPA. FIG. 6A shows that tumors inoculated with virus alone initially exhibited a growth-inhibitory response (from day 7 until day 11 of the experiment). However, by the 16 day time-point these tumors began to rapidly grow. In contrast, the combination of virus and prodrug was extremely effective in producing abrogation of tumor growth throughout the experimental period. In fact, 2/5 tumors completely regressed, 2/5 tumors were completely growth-inhibited, while one tumor appeared to escape treatment. Control tumors treated with control, heat-inactivated virus did not show evidence of growth inhibition during the experimental period (FIG. 6A).

Figure 6B:
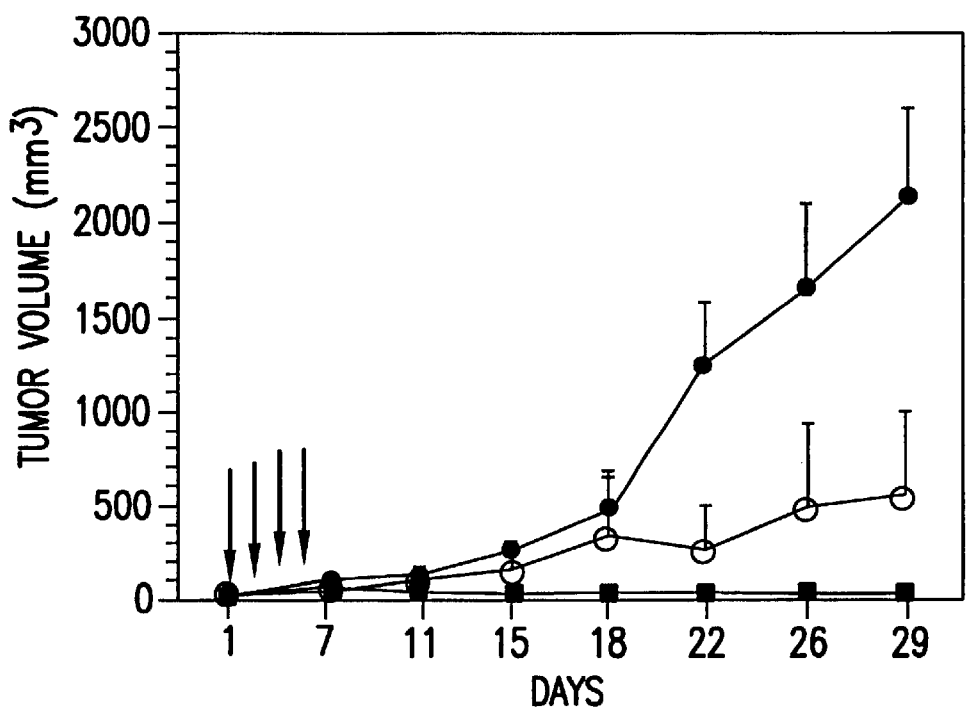
FIG. 6B is a graph depicting the in vivo augmentation of rRp450's oncolytic effect by CPA on U87 tumors. Human U87 tumors were inoculated with CPA (closed circles), rRp450 plus vehicle (open circles), or rRp450 plus CPA (dark squares). The black vertical arrows indicate the times of injection (days 1, 2, 4, and 6). Values represent the average tumor volume from 5 mice per group. Error bars represent the standard error of the mean. For this experiment, differences were statistically significant at the 22, 26 and 29 day time point ($P<0.05$, one way analysis of variance).
Figure 6C:
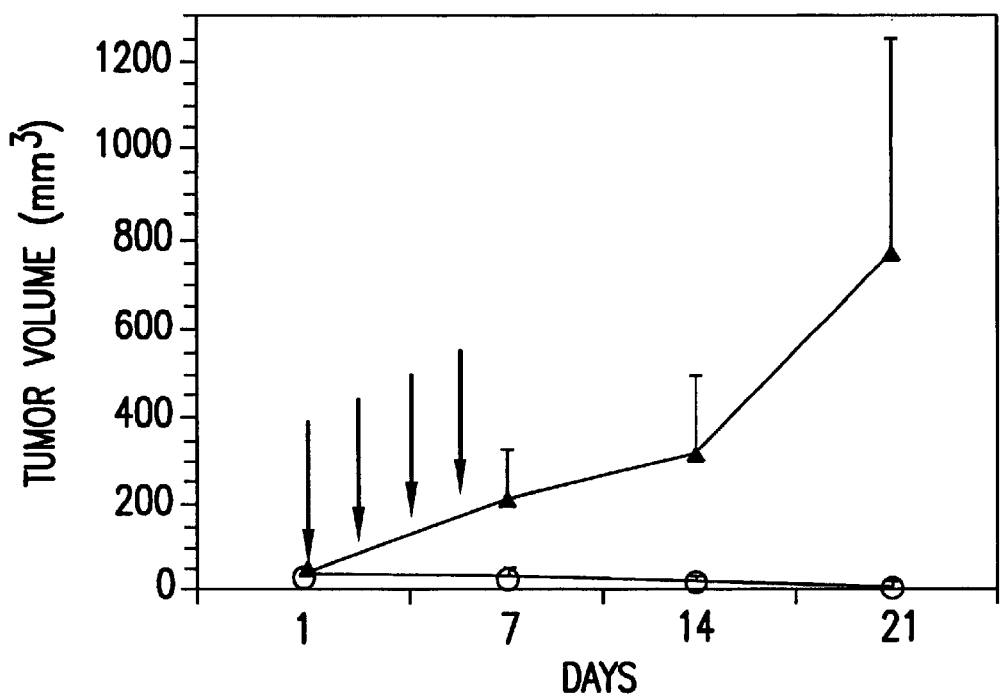
FIG. 6C is a graph comparing the in vivo oncolytic effect on tumors of rRp450 plus CPA to the in vivo oncolytic effect on tumors of replication defective virus plus CPA. Human U87 tumors were inoculated with CPA plus either a replication-defective vector, consisting of an E1-deleted adenoviral vector bearing the CYP2B1 transgene (filled triangles) or rRp450 (open circles). The black verticle arrows represent the days of injection (days 1, 2, 4 and 6). Values represent the average tumor volume from 5 mice per group. Error bars represent the standard error of the mean. For this experiment, differences were statistically significant at the 7, 14 and 21 day time point ($P<0.05$, one way analysis of variance).

A similar experiment was then performed with human U87 glioma cells which were grown in the subcutaneous flank of athymic mice. FIG. 6B shows that the growth of tumors treated with rRp450 plus CPA was completely inhibited. There was complete regression of visible tumor in 4/5 animals, while in the remaining animal there was initial regression of visible tumor followed by growth resumption (results not shown). In contrast, the effect of rRp450 alone on tumor growth was not as dramatic (FIG. 6B). In fact, there was complete regression of visible tumor in 1/5 animal, complete inhibition of tumor growth in 1/5 animals, while the tumors in the remaining 3 animals were only partially inhibited in their growth. Finally, neoplastic growth in control animals treated with intratumoral CPA alone was relatively rapid (FIG. 6B). An additional experiment was then performed to compare tumor regression mediated by rRp450 plus CPA versus that mediated by a replication-defective virus (such as an E1-deleted adenoviral vector bearing the CYP2B1 transgene) plus CPA. FIG. 6C shows that the combination of replication-conditional virus plus prodrug was significantly more effective in producing tumor regression than the combination of replication-defective virus plus CPA.

Virally-treated tumors exhibited evidence of ulceration and necrosis, suggestive of viral replication. To provide evidence for this, tumor tissue was explanted at the 23-day time point and plated onto Vero cells. In both groups, continued viral replication was evident by the presence of numerous plaques (data not shown). Taken in conjunction, these results indicated that the combination of active rRp450 plus CPA could effectively inhibit and, in most cases, produce complete regression of visible rat 9L gliosarcomas and human U87 glioma tumors, without abrogating viral replication.

EXAMPLE 7

In Example 7, the in vivo augmentation by CPA of rRp450's oncolytic effect was further examined, and the use of an implanted polymer to deliver CPA was tested.

Methods and Materials

U87 tumors were treated with rRp450 alone or with CPA in the form of an implanted polymer. Human U87dEGFR tumors ($10^6$ cells S.C.) were established in the subcutaneous flank of athymic mice (NCY/sed, nu/nu; MGH breeding colony). When the tumors reached an approximate size of 200 mm³, using a Hamilton syringe, tumors were injected with rRp450 ($2.5\times10^8$ pfu in a volume of 25 ul), or control virus hrR3 ($10^8$ pfu in a volume of 10 ul), or control virus d120. Tumors in the rRp450 group were also implanted with a polymer containing 1 mg CPA that locally releases CPA, or a polymer that locally releases vehicle. Two mice were used per treatment group. Volume measurements were taken over a period of 30 days using external calipers (Martuza et al., Science 252:854–856 (1991); Mineta et al., Nature Med 1:938–943 (1995); Boviatsis et al., Cancer Res. 54: 5745–5751 (1994)).

Animal studies: Animal studies were performed in accordance with guidelines issued by the Massachusetts General Hospital Subcommittee on Animal Care. Viral inoculation and care of animals harboring viruses were performed in approved viral vector rooms.

Viruses: The hrR3 viral mutant (provided by Dr. Weller (University of Connecticut Medical School, Farmington, Conn.)) consists of an insertion of the lacZ gene into the viral ICP6 locus (Goldstein and Weller, J. Virol. 62: 196–205 (1988)). This generates a mutant that is defective in Hsrr function and that expresses a fusion ICP6-lacZ gene product. The d120 virus is a replication-defective herpes virus (DeLuca et al., *J. Virol.* 56: 558–570 (1985)).

Cell lines: Human U87dEGFR cells were provided by Dr. W. Cavenee (Salk Institute) (Nagane et al., *Cancer Res.* 56. 5079–5086 (1996). Cell lines were maintained in culture in Dulbecco's minimal essential medium supplemented with 10% fetal calf serum, as well as 100 units of penicillin and 0.1 mg of streptomycin per ml of medium (Sigma).

Results

Figure 7:
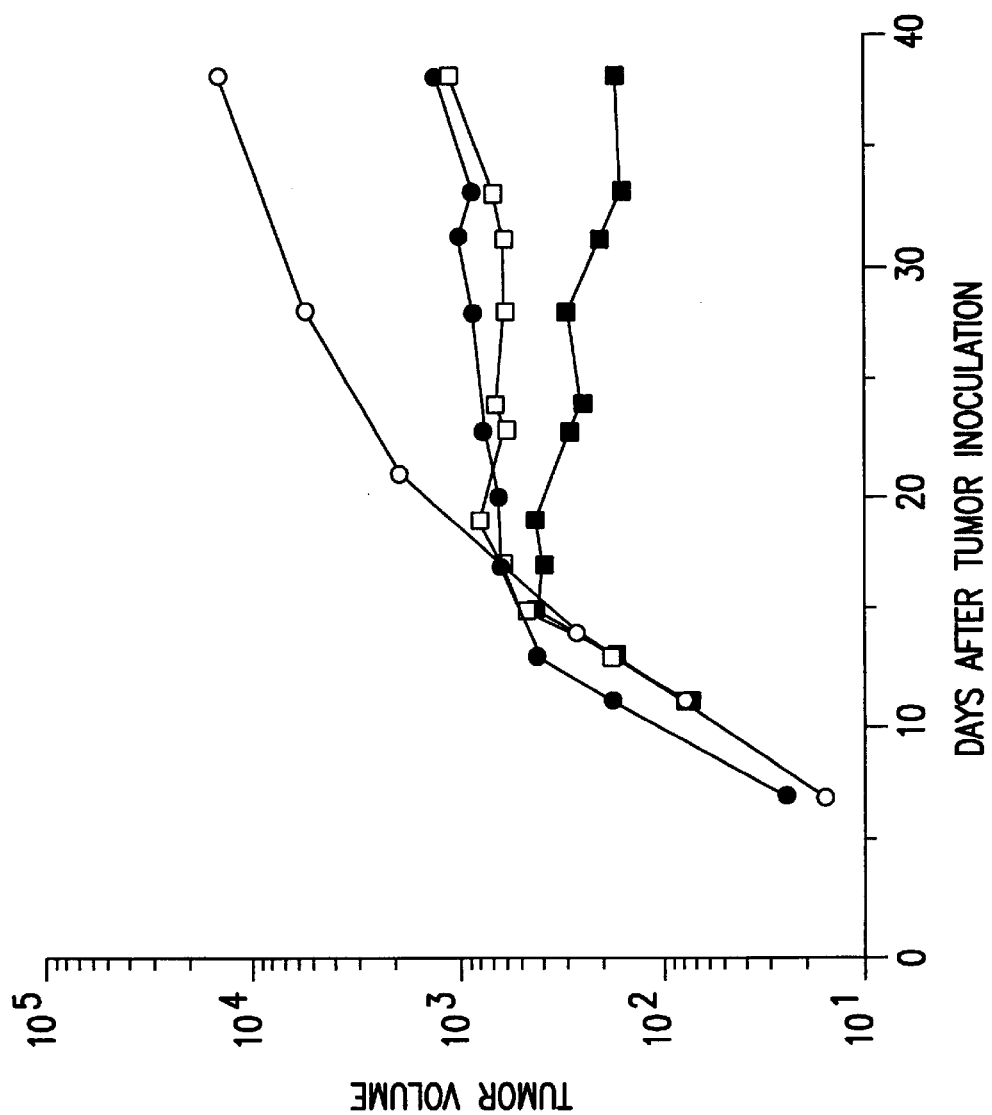
FIG. 7 is a graph depicting the in vivo augmentation of rRp450's oncolytic effect by CPA on U87 tumors. Human glioma tumors (U87dEGFR) were established in the subcutaneous flank of athymic mice. When the tumors reached an approximate size of 200 mm$^3$, they were injected with rRp450 (squares) or control virus: hrR3 (closed circles) or d120 (open circles). Tumors in the rRp450 group were also implanted with a polymer that locally releases cyclophosphamide (closed squares) or that locally releases vehicle (open squares). Tumor volumes were then measured over a period of thirty days. The experiment shows that the combination of rRp450 plus CPA delivered in the form of a polymer (for local release) was more effective than rRp450 plus vehicle delivered in the form of a polymer.

To further determine the in vivo augmentation of rRp450's oncolytic effect by CPA, and to test the use of an implanted polymer to deliver CPA, U87 tumors were treated with rRp450 alone or with CPA in the form of an implanted polymer. The results, as shown in FIG. 7, show that the combination of rRp450 plus CPA delivered in the form of a polymer (for local release) was more effective than rRp450 plus vehicle delivered in the form of a polymer.

EXAMPLE 8

In this example, the effectiveness of two different means of delivering CPA, intratumoral injection and implanted polymer, were compared.

Methods and Materials

Human glioma xenografts ($10^6$ U87dEGFR cells in 100 ul S.C.) were implanted into the skin of athymic mice (NCY/sed, nu/nu; MGH breeding colony) and allowed to reach a volume of approximately 200 mm$^3$. At this time, the tumors were inoculated with HBS and implanted with a polymer containing placebo, or inoculated with HBS and implanted with a polymer containing 1 mg CPA (pCPA), or inoculated with rRp450 ($2.5\times10^8$ pfu in 10 ul HBS) and implanted with pCPA, or inoculated with rRp450 and a bolus of CPA (1 mg), or inoculated with rRp450 and implanted with placebo polymer. Ten mice per treatment group were used. Inoculations of virus (or HBS) and bolus CPA were done on days 0, 2, 4 and 6. Polymers were implanted on day 2. Tumor volume measurements were obtained at 3, 7, 10, 14, 17, 21, 24 and 28 days using external calipers (Martuza et al., *Science* 252:854–856 (1991); Mineta et al., *Nature Med* 1:938–943 (1995); Boviatsis et al., *Cancer Res.* 54: 5745–5751 (1994)). Animals, viruses and cell lines were maintained as described above, and obtained from the sources described above.

Results

Figure 8:
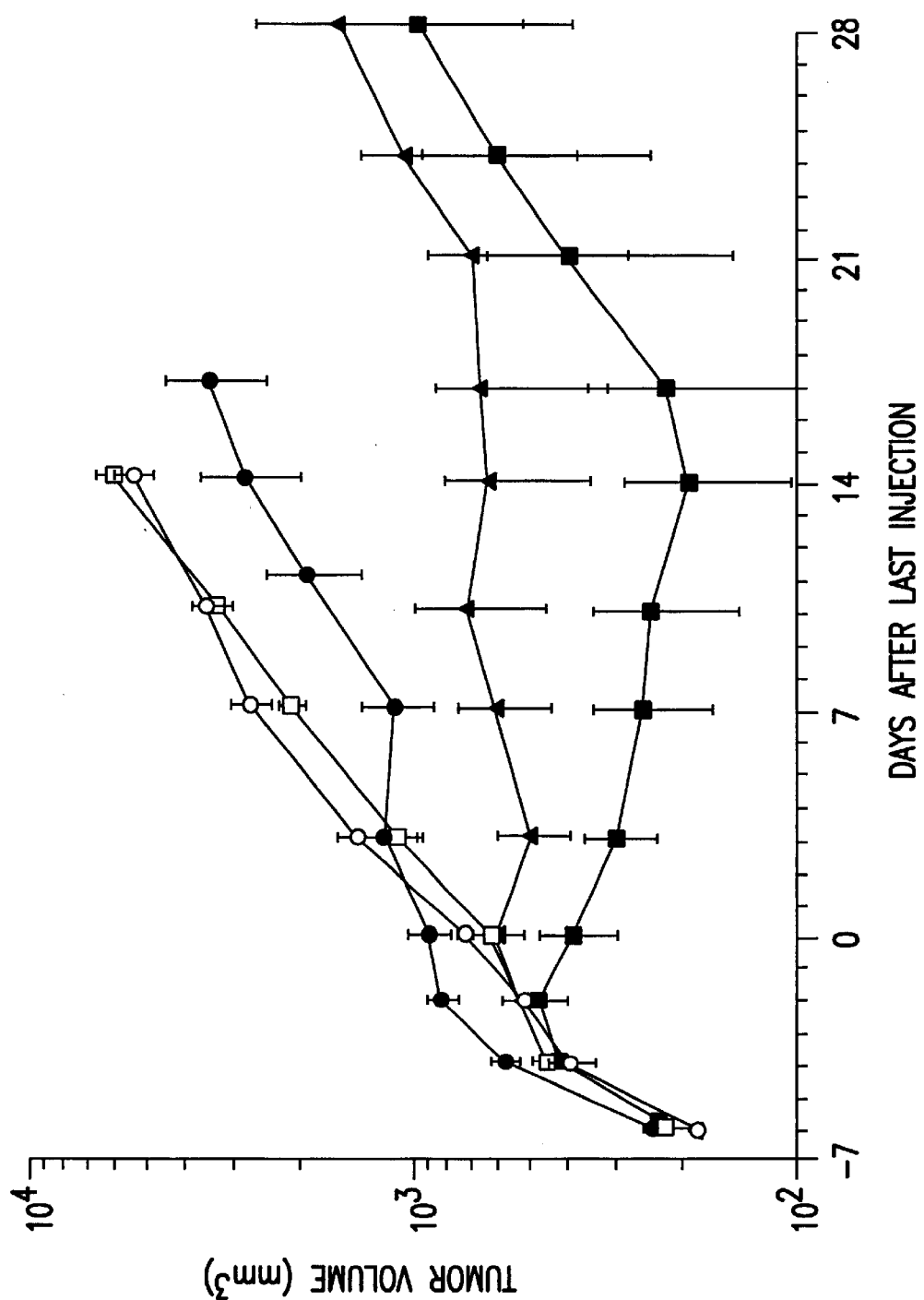
FIG. 8 is a graph comparing the effectiveness of two different means of delivering CPA,. Human glioma (U87dEGFR) xenografts were implanted into the skin of athymic mice and allowed to reach a volume of approximately 200 mm$^3$. At this time, they were inoculated with HBS and implanted with a polymer containing placebo (empty circles), or HBS plus polymer containing CPA (pCPA) (empty squares), or rRp450 plus pCPA (closed squares), or rRp450 plus an injected bolus of CPA (closed triangles), or rRp450 plus placebo polymer (closed circles). As seen in the graph, the most effective treatment for producing inhibition of tumor growth was rRp450 plus pCPA. The next most effective treatment was rRp450 plus CPA delivered by bolus injection.

To compare the effectiveness of two different means of delivering CPA, tumors were inoculated with rRp450, and then CPA was delivered by implantation of a polymer or by intratumoral injection. As demonstrated by the graph in FIG. 8, the most effective treatment for producing inhibition of tumor growth was inoculation with rRp450 plus CPA, where the CPA was delivered by an implanted polymer. The next most effective treatment was rRp450 plus CPA, where the CPA was delivered by injection into the tumor. These results indicate that delivery of 1 mg CPA via an implanted polymer is more effective than four 1 mg doses of CPA via intratumoral injection.

EXAMPLE 9

In Example 9, to compare the effectiveness of two different chemotherapeutic prodrugs, CPA and MCPNU, an experiment similar to that described in Example 8 was performed.

Methods and Materials

Human glioma xenografts ($1\times10^6$ U87dEGFR cells in 100 ul S.C.) were implanted into the skin of athymic mice (NCY/sed, nu/nu; MGH breeding colony), and the tumors were allowed to reach a volume of approximately 200 mm$^3$. At this time, the tumors were inoculated with HBS and implanted with a polymer containing placebo, or inoculated with HBS and implanted with a polymer containing 1 mg CPA (pCPA), or inoculated with rRp450 ($2.5\times10^8$ pfu in a volume of 10 ul) and implanted with placebo polymer, or inoculated with rRp450 and implanted with pCPA, or inoculated with rRp450 and implanted with a polymer containing 5 mg MCPNU (pMCPNU). Ten mice per treatment group were used. Inoculations of virus (or HBS) and bolus CPA were done on days 0, 2, 4 and 6. Polymers were implanted on day 2. Tumor volume measurements were obtained at 3, 7, 10, 14, 17, 21, 24 and 28 days using external calipers (Martuza et al., *Science* 252:854–856 (1991); Mineta et al., *Nature Med* 1:938–943 (1995); Boviatsis et al., *Cancer Res.* 54: 5745–5751 (1994)). Animals, viruses and cell lines were maintained as described above, and obtained from the sources described above.

Results

Figure 9:
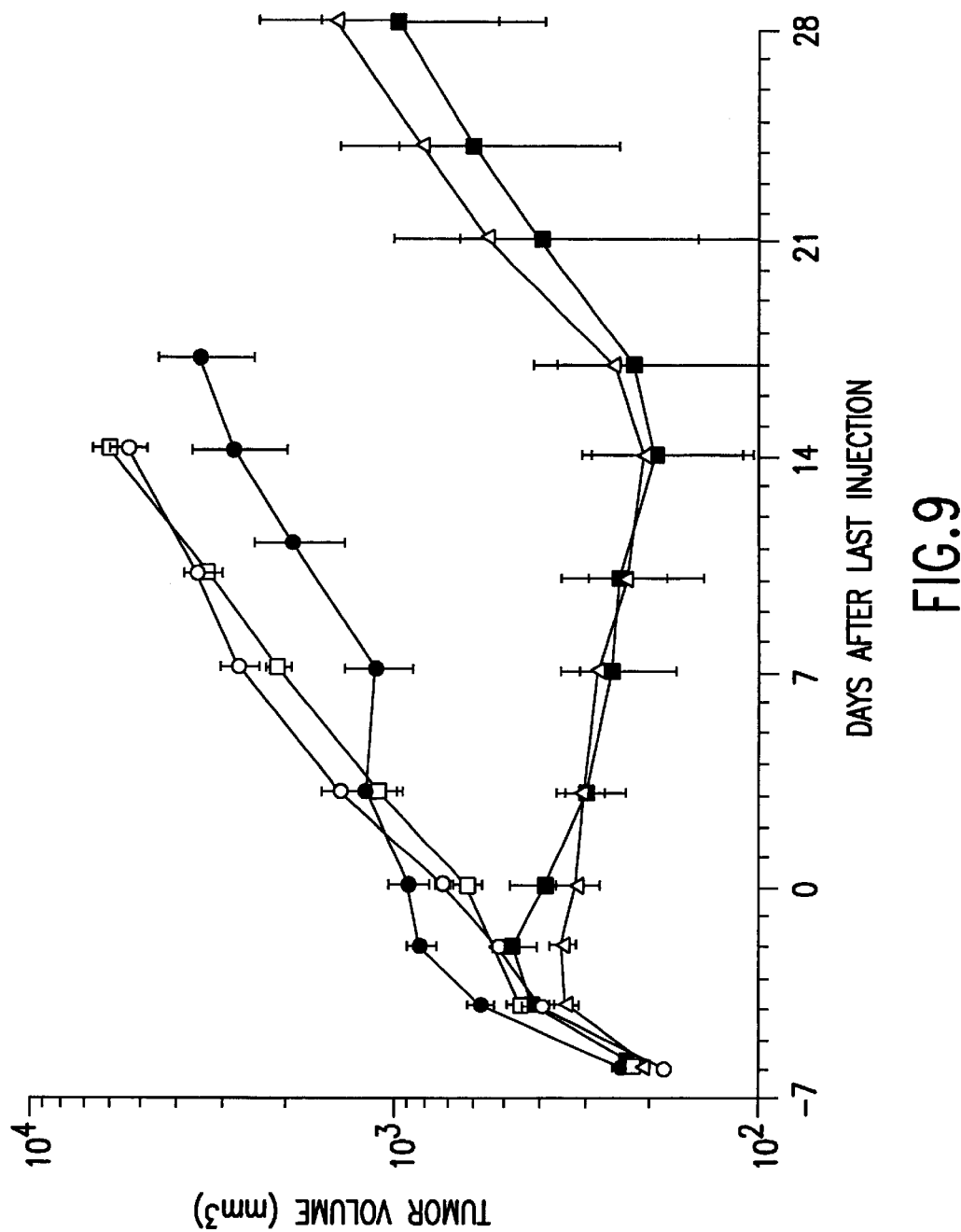
FIG. 9 depicts a graph comparing the effectiveness of CPA to MCPNU, in conjunction with rRp450, in tumor regression. Human glioma (U87dEGFR) xenografts were implanted into the skin of athymic mice. When the tumors reached a volume of approximately 200 mm$^3$, they were inoculated with HBS and implanted with placebo polymer (empty circles), or HBS plus polymer containing CPA (pCPA) (empty squares), or rRp450 plus placebo polymer (closed circles), or rRp450 plus pCPA (closed squares), or rRp450 plus polymer containing MCPNU (pMCPNU) (empty triangles). As seen in the graph, the combination of rRp450 and pMCPNU was as effective at producing tumor regression as the combination of rRp450 and pCPA.

The effectiveness of two different chemotherapeutic prodrugs, CPA and MCPNU, administered in combination with rPp450, were compared. As demonstrated by the graph in FIG. 9, the combination of rRp450 and polymer containing MCPNU was as effective at producing tumor regression as the combination of rRp450 and polymer containing CPA. Thus, overall, the combination of oncolytic virus (rRp450) and prodrug (either CPA or MCPNU) delivered in the form of an implanted polymer provided the most effective treatment against tumors, as compared to oncolytic virus alone, or to oncolytic virus plus prodrug delivered by injection into the tumor.

Discussion

Current anticancer gene therapies have employed either replication-defective viral vectors to deliver an antineoplastic gene (Wei et al., *Human Gene Therapy* 5: 969–978 (1994); Chen and Waxman, *Cancer Res.* 55: 581–589 (1995); Moolten, *Cancer Gene Ther.* 1: 279–287 (1994); Fakhrai et al., *Proc. Natl. Acad. Sci. USA* 93: 2909–2914 (1996); Roth et al., *Nature Med.* 2: 985–991 (1996); Moolten, *Cancer Res.* 46: 5276–5281 (1986); Chen et al., *Proc. Natl. Acad. Sci. USA* 91: 3054–3057 (1994); Mroz, and Moolten, *Hum. Gene Ther.* 4: 589–595 (1993); Mullen et al., *Proc. Natl. Acad. Sci. USA* 59: 33–37 (1992); Wei et al., *Clin. Cancer Res.* 1: 1171–1177 (1995); Marais et al., *Cancer Res.* 56: 4735–4742 (1996); Chen et al., *Cancer Res.* 56: 1331–1340 (1996)), or replication-conditional viruses to selectively lyse the tumor cells (Martuza et al., *Science* 252:854–856 (1991); Mineta et al., *Nature Med* 1:938–943 (1995); Boviatsis et al., *Cancer Res.* 54: 5745–5751 (1994); Kesari, et al., *Lab. Invest.* 73: 636–648 (1995); Chambers et al., *Proc. Natl. Acad. Sci. USA* 92: 1411–1415 (1995); Lorence, R. M. et al., *J. Natl. Cancer. Inst.* 86:1228–1233 (1994); Bischoff, et al., *Science* 274: 373–376 (1996); Rodriguez et al., *Cancer Res.* 57: 2559–2563 (1997)). The viral mutant rRp450 represents the first example of a neoplasm-selective, replication-conditional viral mutant that is also a vector for an established anticancer gene.

The examples above demonstrate that the combined use of this novel viral mutant and of its CYP2B1 transgene produced a significant anticancer effect against tumor cells in culture as well as against tumors established in athymic mice in response to CPA and MCPNU. They also demonstrate the association between expression of mRR in cells and replication of the viral Hsrr mutant. Finally, these examples show that activated CPA metabolites do not affect viral replication, thus permitting the use of this prodrug for cancer therapy without affecting the ability of the virus to spread by replication throughout the treated neoplasm.

The viral mutant rRp450's oncolytic effect correlated with the elevated levels of mammalian ribonucleotide reductase in tumor cells. This enzyme is up-regulated during the $G_1$ phase of the cell cycle and its transcription is regulated by "free" E2F (DeGregori et al., *Mol. Cell. Biol.* 15: 4215–4224 (1995); Lukas et al., *Mol. Cell. Biol.* 16: 1047–1057(1996); Dynlachtetal., *Genes Dev.* 8: 1772–1786 (1994)). E2F appears to be the primary mediator of the cell cycle-regulated transcriptional cascade that involves p 16, cyclin D/cdk4, and pRB (Lukas et al., *Mol. Cell. Biol.* 16:1047–1057(1996); Dynlacht et al., *Genes Dev.* 8:1772–1786 (1994)). The majority of tumors possess an inactivation of one the genes encoding components of this cascade (Ueki et al., *Cancer Res.* 56: 150–153 (1996)), thus liberating E2F and allowing for transcription of mRR (as well as other mammalian enzymes involved in nucleic acid metabolism). Therefore, deletion mutants in viral Hsrr may effectively target a large percentage of neoplastic cells, particularly if they possess a defect in the p16/cyclin D/pRB pathway that leads to an increase in "free" E2F and increased transcription of mRR. The tumor cell lines that we employed in this study (rat 9L, human U87, and human T98 cells) possess inactivating mutations of p16 (Van Meir et al., *Cancer Res.* 54: 649–652 (1994)), as well as elevated levels of mRR. These cells were thus able to complement the replication of rRp450 to levels close to that of the wild-type KOS strain, while neurons with no detectable level of mRR (and with a normal p16 pathway) did not.

It was also important to determine the effect of the converted CPA on viral replication. In previous experiments, the combination of hrR3 and ganciclovir provided a significant anticancer effect in an 9L tumor model. (Boviatsis et al., *Cancer Res.* 54: 5745–5751 (1994)). However, the converted ganciclovir molecules also inhibit viral replication, therefore, use of ganciclovir/thymidine kinase may not be a good selection in this paradigm. The results in the examples show that CPA/CYP2B1, while providing an anticancer effect, does not significantly inhibit viral protein synthesis or viral replication. The explanation for this finding may lie in the mode of action of CPA's active metabolite, phosphoramide mustard (PM). PM produces interstrand and intrastrand crosslinks in the genome of cells: maximum cytotoxicity to cellular DNA is usually achieved during mitosis when multiple DNA strand breaks occur at the cross-link sites (Colvin, in *Cancer Medicine*, Holland et al., eds., Lea and Fabiger, Phila., pub., 1993, at 733–734). Instead, non-mitotic, cross-linked viral DNA may be spared from extensive damage and may be thus be repaired more readily than genomic DNA. Other chemotherapeutic agent/transgene combinations in which the active metabolites would not be expected to significantly inhibit replication of the viral vector include: topoisomerase I or II inhibitors/enzyme with esterase-like activity, such as, e.g., CPT-11/carboxylesterase (Jansen et al., *Int. J Cancer* 70. 335–340 (1997); Danks et al., *Cancer Res.* 58: 20–22 (1998)); CB1954/*E. coli* nitroreductase (Friedlos et al., *Gene Ther.* 5: 105–112 (1998); Green et al., *Cancer Gene Ther.* 4: 229–238 (1997)); 4-ipomeanol/cytochrome P450 4B1 (Verschoyle et al., *Toxicol. Appl. Pharmacol.* 123: 193–198 (1993)); and 2-aminoanthracene/cytochrome P450 4B 1 (Smith et al., *Biochem. Pharmacol.* 50: 1567–1575 (1995)). These chemotherapeutic agent/gene combinations act by inhibiting DNA repair or by DNA-alkylation, respectively.

Unlike CYP2B1, other prodrug-activating enzymes, such as HSV thymidine kinase or *E. coli* cytosine deaminase generate anticancer metabolites that act as "false" nucleotides, producing premature termination of replicating DNA strands. Therefore, these prodrug-activating enzymes would be expected to affect both viral and genomic DNA synthesis and would not be appropriate for use in the invention.

The combination of viral mutant plus CPA was also effective at producing complete regression of subcutaneous rat 9L tumors in athymic mice, and viral mutant plus CPA or MPCNU was effective at producing regression of human U87 tumors in athymic mice. The animal experiments also provided evidence that intratumoral viral replication was still occurring 3 weeks after inoculation of the viral mutant. Clearly, in the group of animals treated with the viral mutant alone, many tumor cells were able to escape the viral oncolytic effect and only the addition of intratumoral prodrug allowed for control of tumor growth.

Moreover, the experiments described above demonstrated that the delivery of the prodrug via an implanted polymer was more effective than by injection. With the advent of polymer technology for local delivery of chemotherapy agents (Gopferich et al., *Pharm. Res.* 11: 1568–1574 (1994)), it would be feasible to treat human tumors with inoculations of rRp450 followed by local implantation of a polymer containing CPA or MCPNU. This would allow intratumoral conversion of the chemotherapeutic agent within the virally-infected tumor cells, bypassing hepatic metabolism and minimizing systemic side-effects. Concerns related to undesirable viral spread outside the tumor target area (for instance, infection of macrophages, endothelial cells, or other cells with potentially up-regulated mRR) could be addressed by treating the host with ganciclovir to stop viral replication.

In conclusion, it is believed that the viral mutant of the invention represents the first example of a viral mutant that can replicate and kill tumor cells, as well as deliver a suicide gene that does not significantly inhibit further viral replication.

Modifications of the above-described modes for carrying out the invention that are obvious to persons of skill in medicine, virology, molecular biology, immunology, pharmacology, and/or related fields are intended to be within the scope of the following claims.

All publications and patents mentioned in this specification are indicative of the level of skill of those skilled in the art to which this invention pertains. All publications and patents are herein incorporated by reference to the same extent as if each individual publication or patent application were specifically and individually indicated to be incorporated by reference.

Although the foregoing invention has been described in some detail by way of illustration and example for purposes of clarity of understanding, it will be obvious that certain changes and modifications can be practiced within the scope of the appended claims.

What is claimed is:

1. A method of killing neoplastic cells in a tumor expressing endogenous ribonucleotide reductase, said method comprising:
   (a) administering directly to a tumor an HSV-1 vector, wherein said HSV-1 vector comprises: a mutation in a ribonucleotide reductase gene of said HSV-1 vector, wherein said ribonucleotide reductase gene is necessary for viral replication and wherein said mutation results in inactivation of said ribonucleotide reductase gene; and a transgene encoding cytochrome P450, wherein said transgene is inserted into said ribonucleotide reductase gene; and
   (b) administering a therapeutically effective amount of a chemotherapeutic agent to said tumor, wherein said chemotherapeutic agent is a chemotherapeutic agent activated by cytochrome P450, and wherein said HSV-1 vector is replicated and said cytochrome P450 is expressed, which activates said therapeutically effective amount of the chemotherapeutic agent.

2. The method of killing neoplastic cells in the tumor of claim 1, wherein said chemotherapeutic agent is selected from the group consisting of cyclophosphamide, ifosfamide, N-methyl cyclophosphamide, methylchloropropylnitrosourea, polymeric cyclophosphamide, polymeric ifosfamide, polymeric N-methyl cyclophosphamide, and polymeric methylchloropropylnitrosourea.

3. The method of killing neoplastic cells in the tumor of claim 1, wherein said ribonucleotide reductase gene encodes the large subunit of ribonucleotide reductase.

4. The method of killing neoplastic cells in the tumor of claim 1, wherein said P450 is P4502B1.

5. The viral vector rRp450.

6. A method of killing neoplastic cells in the tumor expressing endogenous ribonucleotide reductase, said method comprising:
   (a) administering directly to a tumor the viral vector of claim 5; and
   (b) administering a therapeutically effective amount of a chemotherapeutic agent to said tumor, wherein said chemotherapeutic agent is a chemotherapeutic agent activated by cytochrome P450, wherein said viral vector encodes cytochrome P450, and wherein said viral vector is replicated and said cytochrome P450 is expressed, which activates said therapeutically effective amount of the chemotherapeutic agent.

7. The method of killing neoplastic cells in the tumor of claim 6, wherein said chemotherapeutic agent is selected from the group consisting of cyclophosphamide, ifosfamide, N-methyl cyclophosphamide, methylchloropropylnitrosourea, polymeric cyclophosphamide, polymeric ifosfamide, polymeric N-methyl cyclophosphamide, and polymeric methylchloropropylnitrosourea.

8. A method of killing neoplastic cells in the tumor expressing endogenous ribonucleotide reductase, said method comprising:
   (a) administering directly to a tumor an HSV-2 vector, wherein said HSV2 vector comprises: a mutation in a ribonucleotide reductase gene of said HSV-2 vector, wherein said ribonucleotide reductase gene is necessary for viral replication and wherein said mutation results in inactivation of said ribonucleotide reductase gene; and a transgene encoding cytochrome P450, wherein said transgene is inserted into said ribonucleotide reductase gene; and
   (b) administering a therapeutically effective amount of a chemotherapeutic agent to said tumor, wherein said chemotherapeutic agent is a chemotherapeutic agent activated by cytochrome P450, and wherein said HSV-2 vector is replicated and said cytochrome P450 is expressed, which activates said therapeutically effective amount of the chemotherapeutic agent.

9. The method of killing neoplastic cells in the tumor of claim 8, wherein said chemotherapeutic agent is selected from the group consisting of cyclophosphamide, ifosfamide, N-methyl cyclophosphamide, methylchloropropylnitrosourea, polymeric cyclophosphamide, polymeric ifosfamide, polymeric N-methyl cyclophosphamide, and polymeric methylchloropropylnitrosourea.

10. The method of killing neoplastic cells in the tumor of claim 8, wherein said ribonucleotide reductase gene encodes the large subunit of ribonucleotide reductase.

11. The method of killing neoplastic cells in the tumor of claim 8, wherein said P450 is P4502B1.

12. A method of killing neoplastic cells in the tumor expressing endogenous thymidine kinase, said method comprising:
   (a) administering directly to a tumor an HSV-1 vector, wherein said HSV-1 vector comprises: a mutation in a thymidine kinase gene of said HSV-1 vector, wherein said thymidine kinase gene is necessary for viral replication and wherein said mutation results in inactivation of said thymidine kinase gene; and a transgene encoding cytochrome P450, wherein said transgene is inserted into said thymidine kinase gene; and
   (b) administering a therapeutically effective amount of a chemotherapeutic agent to said tumor, wherein said chemotherapeutic agent is a chemotherapeutic agent activated by cytochrome P450, and wherein said HSV-1 vector is replicated and said cytochrome P450 is expressed, which activates said therapeutically effective amount of the chemotherapeutic agent.

13. The method of killing neoplastic cells in the tumor of claim 12, wherein said chemotherapeutic agent is selected from the group consisting of cyclophosphamide, ifosfamide, N-methyl cyclophosphamide, methylchloropropylnitrosourea, polymeric cyclophosphamide, polymeric ifosfamide, polymeric N-methyl cyclophosphamide, and polymeric methylchloropropylnitrosourea.

14. The method of killing neoplastic cells in the tumor of claim 12, wherein said P450 is P4502B1.

15. A method of killing neoplastic cells in a tumor expressing endogenous thymidine kinase, said method comprising:
  (a) administering directly to a tumor an HSV-2 vector, wherein said HSV-2 vector comprises: a mutation in a thymidine kinase gene of said HSV-2 vector, wherein said thymidine kinase gene is necessary for viral replication and wherein said mutation results in inactivation of said thymidine kinase gene; and a transgene encoding cytochrome P450, wherein said transgene is inserted into said thymidine kinase gene; and
  (b) administering a therapeutically effective amount of a chemotherapeutic agent to said tumor, wherein said chemotherapeutic agent is a chemotherapeutic agent activated by cytochrome P450, and wherein said HSV-2 vector is replicated and said cytochrome P450 is expressed, which activates said therapeutically effective amount of the chemotherapeutic agent.

16. The method of killing neoplastic cells in the tumor of claim 15, wherein said chemotherapeutic agent is selected from the group consisting of cyclophosphamide, ifosfamide, N-methyl cyclophosphamide, methylchloropropyl-nitrosourea, polymeric cyclophosphamide, polymeric ifosfamide, polymeric N-methyl cyclophosphamide, and polymeric methylchloropropylnitrosourea.

17. The method of killing neoplastic cells in the tumor of claim 15, wherein said P450 is P4502B1.

18. A method of killing neoplastic cells in a tumor expressing endogenous ribonucleotide reductase, said method comprising:
  (a) administering directly to a tumor an HSV vector, wherein said HSV vector comprises: a mutation in a ribonucleotide reductase gene of said HSV vector, wherein said ribonucleotide reductase gene is necessary for viral replication and wherein said mutation results in inactivation of said ribonucleotide reductase gene; and a transgene encoding cytochrome P450, wherein said transgene is inserted into said ribonucleotide reductase gene; and
  (b) administering a therapeutically effective amount of a chemotherapeutic agent to said tumor, wherein said chemotherapeutic agent is a chemotherapeutic agent activated by cytochrome P450, and wherein said HSV vector is replicated and said cytochrome P450 is expressed, which activates said therapeutically effective amount of the chemotherapeutic agent.

19. The method of killing neoplastic cells in the tumor of claim 18, wherein said chemotherapeutic agent is selected from the group consisting of cyclophosphamide, ifosfamide, N-methyl cyclophosphamide, methylchloropropyl-nitrosourea, polymeric cyclophosphamide, polymeric ifosfamide, polymeric N-methyl cyclophosphamide, and polymeric methylchloropropylnitrosourea.

20. The method of killing neoplastic cells in the tumor of claim 18, wherein said ribonucleotide reductase gene encodes the large subunit of ribonucleotide reductase.

21. The method of killing neoplastic cells in the tumor of claim 18, wherein said P450 is P4502B1.

22. A method of killing neoplastic cells in a tumor expressing endogenous thymidine kinase, said method comprising:
  (a) administering directly to a tumor an HSV vector, wherein said HSV vector comprises: a mutation in a thymidine kinase gene of said HSV vector, wherein said thymidine kinase gene is necessary for viral replication and wherein said mutation results in inactivation of said thymidine kinase gene; and a transgene encoding cytochrome P450, wherein said transgene is inserted into said thymidine kinase gene; and
  (b) administering a therapeutically effective amount of a chemotherapeutic agent to said tumor, wherein said chemotherapeutic agent is a chemotherapeutic agent activated by cytochrome P450, and wherein said HSV vector is replicated and said cytochrome P450 is expressed, which activates said therapeutically effective amount of the chemotherapeutic agent.

23. The method of killing neoplastic cells in a tumor of claim 22, wherein said chemotherapeutic agent is selected from the group consisting of cyclophosphamide, ifosfamide, N-methyl cyclophosphamide, methylchloropropyl-nitrosourea, polymeric cyclophosphamide, polymeric ifosfamide, polymeric N-methyl cyclophosphamide, and polymeric methylchloropropylnitrosourea.

24. The method of killing neoplastic cells in a tumor of claim 22, wherein said P450 is P4502B1.

25. A method of killing neoplastic cells in a tumor expressing endogenous ribonucleotide reductase, said method comprising:
  (a) administering directly to a tumor an HSV vector, wherein said HSV vector comprises: a mutation in a ribonucleotide reductase gene of said HSV vector, wherein said ribonucleotide reductase gene is necessary for viral replication and wherein said mutation results in inactivation of said ribonucleotide reductase gene; and a transgene encoding carboxylesterase; and
  (b) administering a therapeutically effective amount of a chemotherapeutic agent to said tumor, wherein said chemotherapeutic agent is a chemotherapeutic agent activated by carboxylesterase, and wherein said HSV vector is replicated and said carboxylesterase is expressed, which activates said therapeutically effective amount of the chemotherapeutic agent.

26. The method of killing neoplastic cells of claim 25, wherein said chemotherapeutic agent is CPT-11.

27. The method of killing neoplastic cells of claim 25, wherein said HSV vector is an HSV-1 vector.

28. The method of killing neoplastic cells of claim 27, wherein said chemotherapeutic agent is CPT-11.

29. The method of killing neoplastic cells of claim 25, wherein said HSV vector is an HSV-2 vector.

30. The method of killing neoplastic cells in a tumor of claim 29, wherein said chemotherapeutic agent is CPT-11.

* * * * *

SEQUENCE LISTING

<160> NUMBER OF SEQ ID NOS: 7

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: DNA primer

<400> SEQUENCE: 1
atggttcaca cgcacgtctt c                                              21

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: DNA primer

<400> SEQUENCE: 2
ggtcctggtg ggaagttgc                                                 19

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: DNA primer

<400> SEQUENCE: 3
tgtcactcgt tgttcgttga c                                              21

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: DNA primer

<400> SEQUENCE: 4
gcgcctgatt cgccacctgg acg                                            23

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: DNA primer

<400> SEQUENCE: 5
gagctggctc ttgatcac                                                  18

<210> SEQ ID NO 6
<211> LENGTH: 16
<212> TYPE: DNA
<213> ORGANISM: Artificial Sequence
<220> FEATURE:
<223> OTHER INFORMATION: Description of Artificial Sequence: DNA primer

<400> SEQUENCE: 6
tcgctgtgat tgagcc                                                    16

<210> SEQ ID NO 7
<211> LENGTH: 22

```
-continued
<212> TYPE: DNA
<213> ORGANISM: Artificial Sequence
<220> FEATURE:
<223> OTHER INFORMATION: Description of Artificial Sequence: DNA primer

<400> SEQUENCE: 7
gcttcgacgg gagaggatgc gg                                              22
```